US012766316B2

(12) United States Patent
Nguyen et al.

(10) Patent No.: US 12,766,316 B2
(45) Date of Patent: Oct. 20, 2026

(54) IMPLANTABLE PIEZOELECTRIC SCAFFOLD AND EXERCISE-INDUCED PIEZOELECTRIC STIMULATION

(71) Applicant: University of Connecticut, Farmington, CT (US)

(72) Inventors: Thanh Duc Nguyen, South Windsor, CT (US); Yang Liu, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 276 days.

(21) Appl. No.: 18/687,244

(22) PCT Filed: Sep. 7, 2022

(86) PCT No.: PCT/US2022/042749
§ 371 (c)(1),
(2) Date: Feb. 27, 2024

(87) PCT Pub. No.: WO2023/038966
PCT Pub. Date: Mar. 16, 2023

(65) Prior Publication Data

US 2024/0399144 A1 Dec. 5, 2024

Related U.S. Application Data

(60) Provisional application No. 63/242,660, filed on Sep. 10, 2021.

(51) Int. Cl.
*A61N 1/32* (2006.01)
*A61N 1/05* (2006.01)
(Continued)

(52) U.S. Cl.
CPC ............... *A61N 1/326* (2013.01); *A61N 1/05* (2013.01); *H10N 30/078* (2023.02); *H10N 30/50* (2023.02); *H10N 30/702* (2024.05)

(58) Field of Classification Search
CPC ........ A61N 1/326; A61N 1/05; A61F 2/30756
See application file for complete search history.

(56) References Cited

U.S. PATENT DOCUMENTS

2014/0145365 A1 5/2014 Omenetto et al.
2017/0119931 A1 5/2017 Arinzeh et al.
(Continued)

FOREIGN PATENT DOCUMENTS

WO 2009108705 A1 3/2009
WO 2019195264 A1 10/2019

OTHER PUBLICATIONS

Extended European Search Report issued by the European Patent Office for Application No. 22867995.7-1109, dated Jun. 26, 2025.
(Continued)

*Primary Examiner* — Carl H Layno
*Assistant Examiner* — Bryan Mcallister Lee
(74) *Attorney, Agent, or Firm* — Cowan, Liebowitz & Latman, P.C.; Daniel J. Gross

(57) ABSTRACT

An implantable scaffold is provided including multiple piezoelectric films and at least one compressible intervening layer. A first of the piezoelectric films is on a first side of the compressible intervening layer and a second of the plurality of piezoelectric films is on a second side of the compressible intervening layer opposite the first piezoelectric film. Upon applying a mechanical force to the first piezoelectric film, the first piezoelectric film deforms towards the second piezoelectric film. Also provided is a method of treatment leveraging the implantable scaffold.

13 Claims, 18 Drawing Sheets

(51) Int. Cl.
*H10N 30/00* (2023.01)
*H10N 30/078* (2023.01)
*H10N 30/50* (2023.01)

(56) References Cited

U.S. PATENT DOCUMENTS

| | | | |
|---|---|---|---|
| 2017/0355954 A1 | 12/2017 | Scott Carnell et al. | |
| 2018/0206995 A1 | 7/2018 | Kang | |
| 2019/0341541 A1 | 11/2019 | Yoshida et al. | |
| 2020/0276018 A1* | 9/2020 | Nguyen .................. | A61L 27/56 |
| 2021/0127998 A1 | 5/2021 | Nguyen et al. | |

OTHER PUBLICATIONS

International Search Report issued by the ISA/US for International Patent Application No. PCT/US 22/42749, mailed on Feb. 14, 2023.
First Examination Report issued by the Intellectual Property Office of India for Indian Patent Application No. 202417028757, dated Mar. 17, 2026.

* cited by examiner

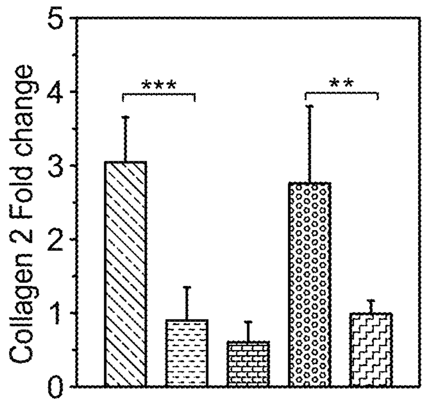
FIG.14A
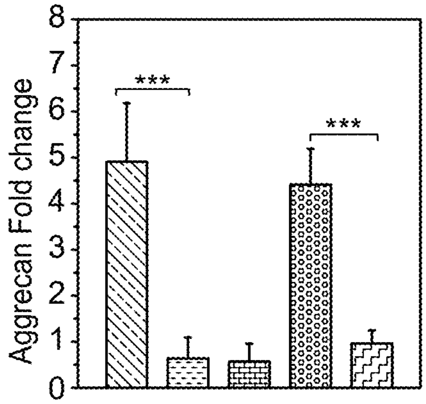
FIG.14B
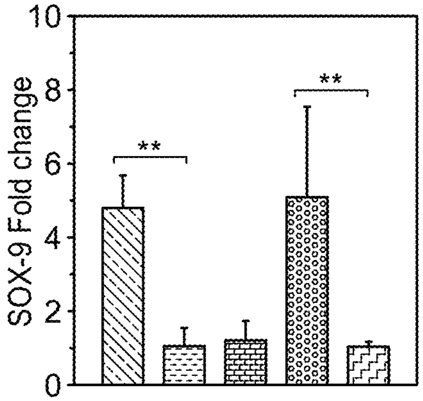
FIG.14C
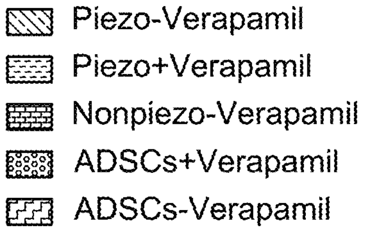

IMPLANTABLE PIEZOELECTRIC SCAFFOLD AND EXERCISE-INDUCED PIEZOELECTRIC STIMULATION

CROSS-REFERENCE TO RELATED APPLICATION

This application is the U.S. national stage entry, under 35 U.S.C. § 371, of International Application No. PCT/US2022/042749, filed Sep. 7, 2022, which claims the benefit of U.S. Provisional Patent Application No. 63/242,660, filed Sep. 10, 2021, the entire contents of each of which are hereby incorporated by reference.

STATEMENT OF GOVERNMENT SUPPORT

This invention was made with government support under Grant No. EB024787 from the National Institutes of Health. The government has certain rights in the invention.

FIELD OF THE INVENTION

The invention described herein is directed to exercise-induced piezoelectric stimulation for cartilage regeneration.

BACKGROUND

Every year, millions of Americans undergo total knee replacement principally due to osteoarthritis (OA). Current medical therapies are focused on anti-inflammatory or pain-relieving drugs, which only alleviate symptoms, but do not cure the disease. The use of growth factors yields many adverse effects while stem-cell therapy needs further investigation relative to efficacy and safety issues. The surgical approach to the treatment of cartilage defects has been focused on using transplanted replacement tissue grafts. Despite many advantages, replacement auto- and allo-grafts pose several problems. These include donor site morbidity, infection, immune reactions and in particular, limits in supply.

Consequently, artificial "engineered" cartilage grafts constructed in vitro by using synthetic biomaterial scaffolds have received considerable attention. However, their widespread use is also limited due to the inefficiency of generating hyaline cartilage after implantation. Such grafts often fail to become load bearing in normal cartilage tissues and easily break down under repeated joint forces. As such, it is necessary to seek a new approach that can effectively stimulate and accelerate cartilage growth.

Cartilage is sensitive to electrical field/current/charge stimulation. Battery-based and bimetallic electrodes have been used to generate nano-ampere current to stimulate the growth of hyaline cartilage in rabbit knees. Electrical fields are reported to stimulate the expression of typical genes and proteins regulating articular cartilages in vitro. Both direct and alternative currents have been utilized to generate stimulation; biphasic currents have been shown to repair hyaline cartilage in male rats. There are several review papers on research using electrical stimulation (ES) for bone and cartilage growth. As bioelectrical signals are ubiquitous inside the body, ES is considered a natural source for promoting tissue regeneration.

However, current devices used for ES still struggle with limitations, rendering the method impractical for clinical use. As a drawback, externally generated electromagnetic fields used as non-invasive stimulators in the knee joint, are drastically attenuated. Devices directly implanted inside the joint avoids the problem of tissue absorption. However, they usually contain non-biodegradable materials and toxic batteries that require invasive procedures to remove. This can readily damage the healing tissue.

There is a need for implantable devices that are biodegradable and avoid the need for batteries while still providing effective electrical stimulation in the context of therapy.

SUMMARY

A biodegradable piezoelectric (poly (L-lactic acid)) (PLLA) scaffold under applied force can act as a battery-less electrical stimulator to promote chondrogenic differentiation of stem cells in vitro and cartilage regeneration. PLLA can be also replaced with other biodegradable materials such as silk or polyglycine, fabricated in the same manner (e.g. electrospinning or thermal-stretching) to be deployed with piezoelectricity.

Disclosed herein is a wireless, battery-free and self-stimulated technology to generate electrical stimulation for inducing cartilage regeneration. Also provided is a tool to systematically study interaction between stem-cells and surface charge for cartilage regeneration, and an approach to design and create a novel nanomaterial-based biodegradable piezoelectric scaffolds which can form highly-regenerative replacement for treatment of osteoarthritis.

Accordingly, the present disclosure provides a piezoelectric scaffold which is safe, biodegradable, highly chondrogenic to provide an optimal treatment for osteoarthritis (OA). The stimulation is induced by the exercise/movement and therefore no outside treatment is needed. The surface charge will be produced and fine-tuned by multi-layer structure in combination with collagen hydrogel and the exercise/movement. Accordingly, polarized charges are generated from the piezoelectric materials, and such piezoelectric materials can be used in a combination with exercise and other movement to create a highly chondrogenic effects.

The nanomaterial-based scaffold allows one to easily obtain different mechanical strength, pore-size and flexibility by tuning the layer structure and fabrication/processing-conditions to create the optimal charges suitable for cartilage regeneration. Accordingly, the proposed scaffold can be tuned, thereby providing excellent control over various properties in a manner that has not been achieved in conventional biomaterials for cartilage regeneration.

Finally, the PLLA nanofiber membrane can be simply made by electrospinning and the scaffold can be easily fabricated. All the materials (PLLA and collagen hydrogel) have been shown to be biodegradable and safe for use in many FDA approved and/or CE marked medical implants. As such this is a very highly translational biomaterial which could obtain a quick FDA approval for clinical use.

Thus, a combination of many novel concepts, including charge-induced cartilage regeneration, and new approaches, such as combining surface charge and physical stimulation from exercise/movement to enhance/induce cartilage growth, along with the use of a biodegradable piezoelectric nanomaterial-based scaffold with highly tunable mechanical/degradation properties creates a powerful, highly controllable scaffold for treating osteoarthritis (OA).

Accordingly, in some embodiments, an implantable scaffold is provided including a plurality of piezoelectric films and at least one compressible intervening layer. A first of the plurality of piezoelectric films is on a first side of the compressible intervening layer and a second of the plurality of piezoelectric films is on a second side of the compressible intervening layer opposite the first piezoelectric film.

Upon applying a mechanical force to the first piezoelectric film, the first piezoelectric film deforms towards the second piezoelectric film.

In some embodiments, the plurality of piezoelectric films are biodegradable, and such implantable scaffold does not include a battery. Similarly, such a scaffold may not be implanted with a battery.

In some such embodiments, each of the plurality of piezoelectric films comprise at least one of poly (L-lactic acid) (PLLA), silk, polyglycine, or collagen. Typically, each of the plurality of piezoelectric films are manufactured by electrospinning.

In some such embodiments, the plurality of piezoelectric films are each manufactured by dispensing a solvent from a needle in an electric field to deposit nanofibers onto a drum rotating at a speed sufficient so as to mechanically stretch and align the nanofibers. In some such embodiments, each of the plurality of piezoelectric films therefore comprises nanofibers substantially aligned with each other.

In embodiments having substantially aligned nanofibers, the method may further comprise three piezoelectric films arranged as substantially parallel planes with a third piezoelectric film being between the first and second piezoelectric film. The at least one compressible intervening layer is then a two compressible intervening layers, with a first one between the first piezoelectric film and the third piezoelectric film and a second compressible intervening layer between the second piezoelectric film and the third piezoelectric film.

In some such embodiments, the substantially aligned nanofibers of the first piezoelectric film are substantially parallel with the substantially aligned nanofibers of the second piezoelectric film, and are substantially perpendicular with the substantially aligned nanofibers of the third piezoelectric film.

In some embodiments, the piezoelectric films each have a first side manufactured on a surface of a drum and a second side manufactured facing away from the drum. In some such embodiments, the first side of at least one of the piezoelectric films faces towards the compressible intervening layer. In some such embodiments, each of the outer piezoelectric films are positioned with their first sides facing the compressible intervening layer.

Similarly, in some embodiments, each of the piezoelectric films has a first side for generating a positive electrical charge and a second side for generating a negative electrical charge. The first side of at least one of the piezoelectric films, and in some embodiments, both of the piezoelectric films, then faces the compressible intervening layer.

In some embodiments, the compressible intervening layer is a hydrogel. Such a hydrogel may be collagen.

Also provided is a method of treatment leveraging the device described herein. In some a method, a cartilage or bone defect to be treated is first identified. Following such an identification, the method provides an implantable scaffold comprising a plurality of piezoelectric films and at least one compressible intervening layer between at least two of the plurality of piezoelectric films.

The method then proceeds with implanting the implantable scaffold adjacent the cartilage or bone defect to be treated, and within a pinch point of a joint.

The method then proceeds with providing an exercise protocol for generating periodic impact at the pinch point, such that the periodic impact applies a mechanical force to a first piezoelectric film of the plurality of piezoelectric films, such that the first piezoelectric film compresses the compressible layer and deforms towards the second piezoelectric film.

In some such methods, each of the piezoelectric films has a first side for generating a positive electrical charge and a second side for generating a negative electrical charge. After implanting the implantable scaffold, the second side of the first piezoelectric film faces the cartilage or bone defect to be treated.

In some embodiments, the piezoelectric films are biodegradable and no battery is implanted with the implantable scaffold.

In some such embodiments, each of the plurality of piezoelectric films comprise at least one of poly (L-lactic acid) (PLLA), silk, polyglycine, or collagen. The plurality of piezoelectric films may be manufactured by dispensing a solvent from a needle in an electric field to deposit nanofibers on a surface. After manufacturing, the nanofibers of each of the plurality of piezoelectric films are substantially aligned.

In some such embodiments, the plurality of piezoelectric films is three piezoelectric films arranged as substantially parallel planes. The third piezoelectric film is then located between the first and second piezoelectric film. The at least one compressible intervening layer is then a first compressible intervening layer between the first piezoelectric film and the third piezoelectric film and a second compressible intervening layer between the second piezoelectric film and the third piezoelectric film.

In some such embodiments, the substantially aligned nanofibers of the first piezoelectric film are substantially parallel with the substantially aligned nanofibers of the second piezoelectric film, and are substantially perpendicular with the substantially aligned nanofibers of the third piezoelectric film.

In some embodiments the compressible intervening layer is a hydrogel. Such a hydrogel may be collagen.

In some embodiments, the cartilage or bone defect to be treated is in a knee joint and the exercise protocol is a walking protocol for generating periodic impact at the knee joint.

In some embodiments, upon identifying the cartilage or bone defect to be treated and prior to providing the implantable scaffold, at least one characteristic of the implantable scaffold is selected based on a characteristic of a patient in which the cartilage or bone defect was identified.

In some such embodiments, at least one of a porosity of nanofibers of the plurality of piezoelectric films, a number of compressible intervening layers, and a thickness of at least one of the compressible intervening layers is selected based on a weight of the patient to tune the implantable scaffold.

BRIEF DESCRIPTION OF THE DRAWINGS

FIGS. 14A-C illustrate an expression of chondrogenic genes Collagen type II, Aggrecan and SOX-9 after 14 days culture of ADSCs under the piezoelectric stimulation (i.e. piezo scaffold+pressure) with or without the VGCC inhibitor Verapamil.

DETAILED DESCRIPTION OF THE PREFERRED EMBODIMENTS

Figure 1:
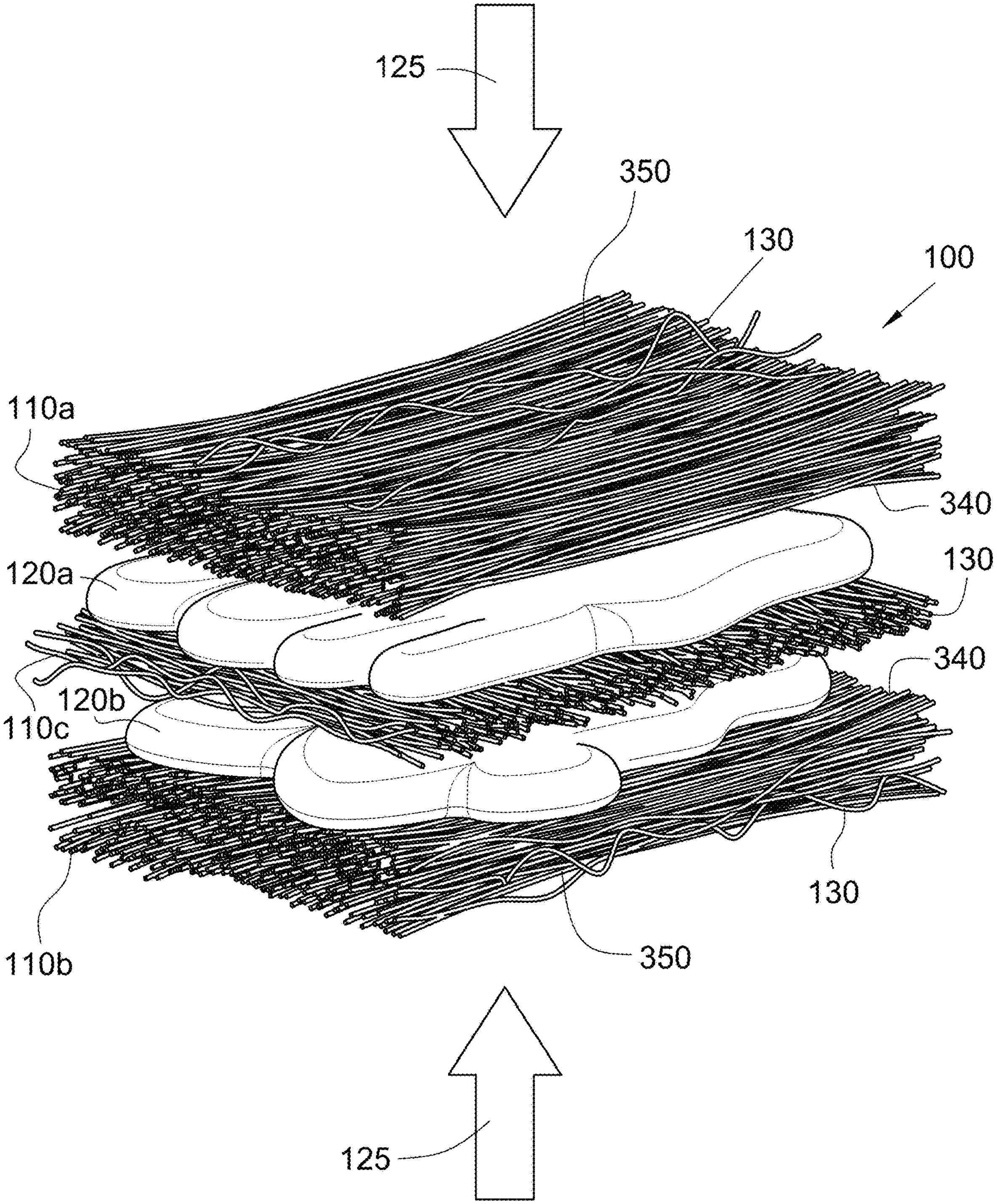
FIG. 1 is an implantable scaffold in accordance with this disclosure.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper." "horizontal." "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached." "affixed," "connected," "coupled." "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

It is important to note that the embodiments disclosed are only examples of the many advantageous uses of the innovative teachings herein. In general, statements made in the specification of the present application do not necessarily limit any of the various claimed disclosures. Moreover, some statements may apply to some inventive features but not to others. In general, unless otherwise indicated, singular elements may be in plural and vice versa with no loss of generality.

Figure 2:
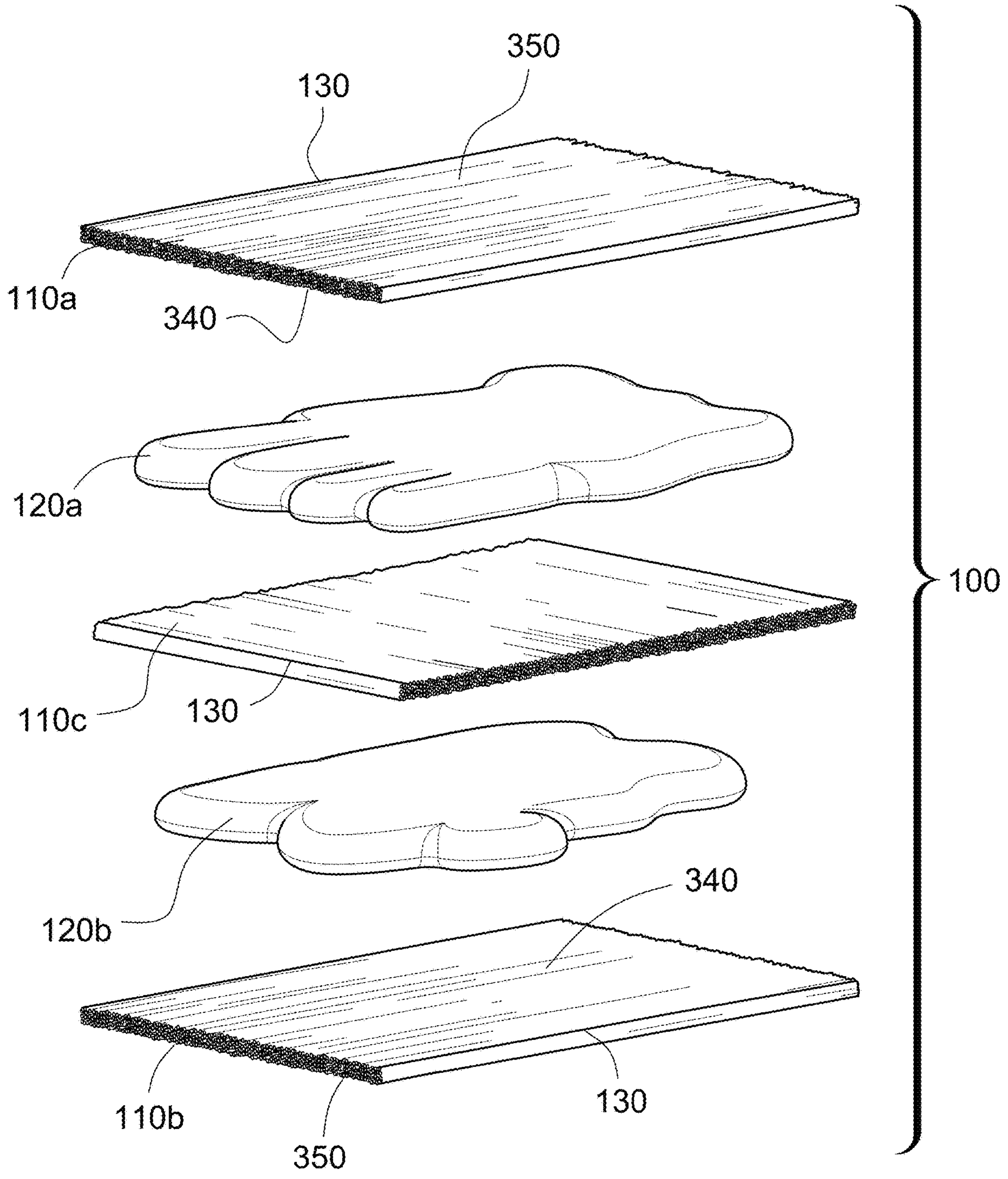
FIG. 2 is an exploded view of the scaffold of FIG. 1.
Figure 5A:
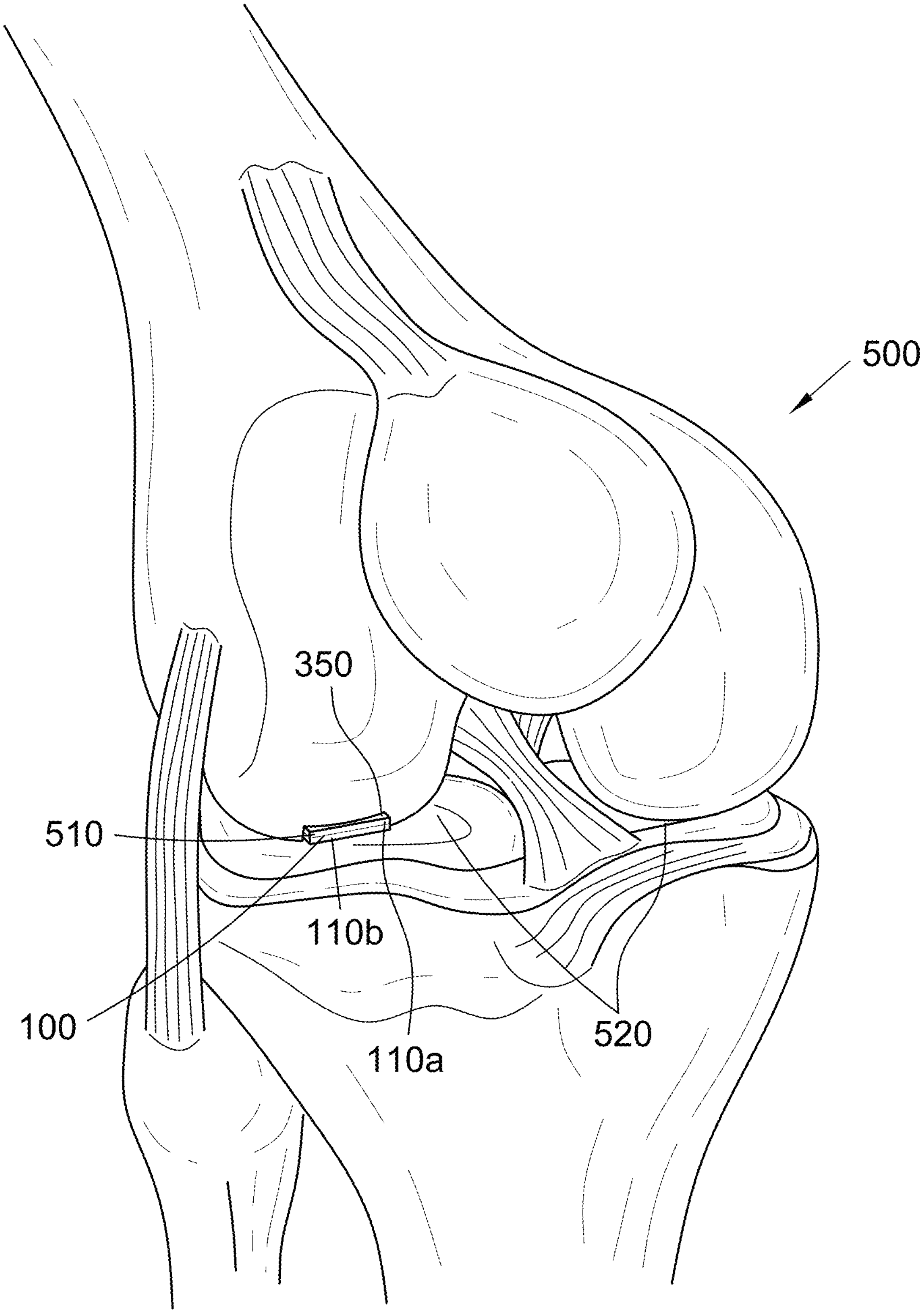
FIG. 5A is an image of the implantable scaffold of FIG. 1 embedded in a user's knee.
Figure 5B:
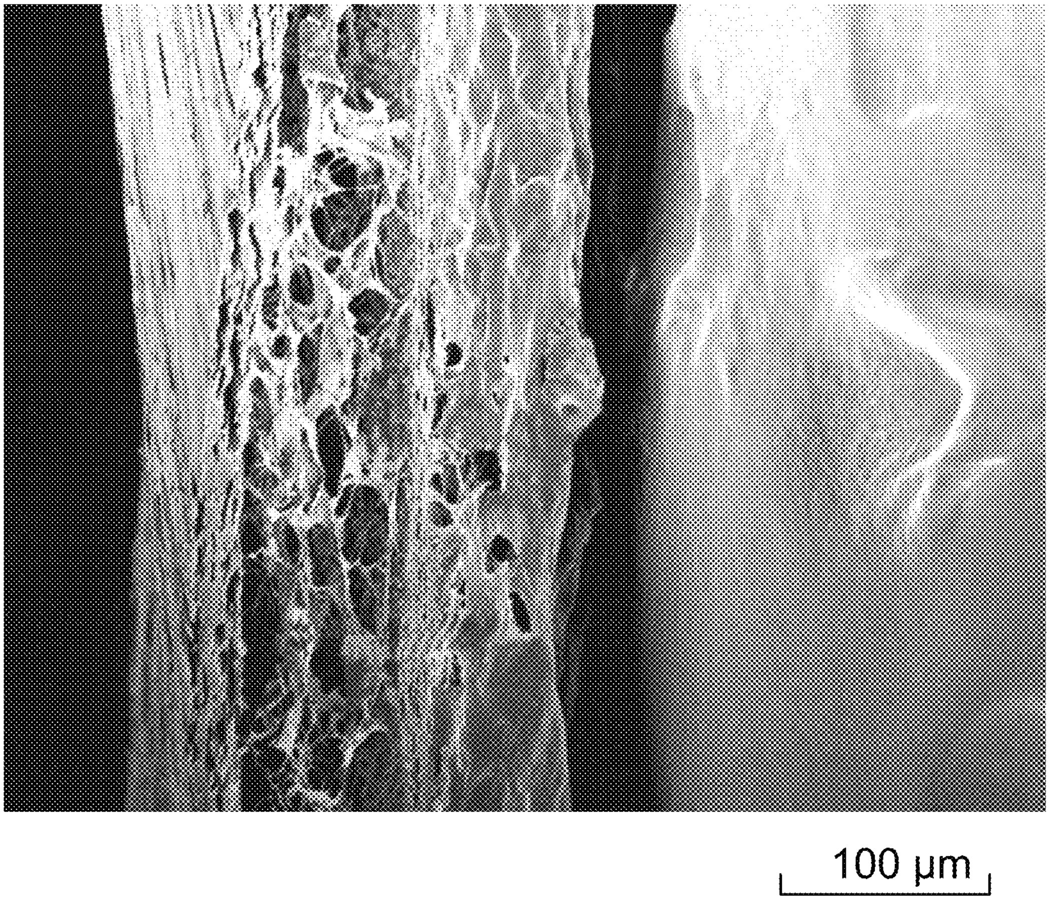
FIG. 5B is a scanning electron microscope (SEM) image of the implantable scaffold adjacent an osteochondral defect.

FIG. 1 is an implantable scaffold 100 in accordance with this disclosure. FIG. 2 is an exploded view of the scaffold 100 of FIG. 1. It is noted that in this discussion, the terms scaffold and implant are sometimes used interchangeably. The scaffold 100 shown is often implanted directly into a patient such as, for example, at the knee 500, as shown in FIG. 5. In some embodiments, the scaffold 100 may be integrated into a larger implant, while in other embodiments, the scaffold itself may be the implant. It is further noted that the user of the scaffold 100 or implant in the description that follows is typically the patient, and as such, the scaffold is implanted into the patient's, or user's, knee 500. Such terms are similarly used interchangeably.

As shown, the scaffold includes a plurality of piezoelectric films 110*a, b, c* and at least one compressible intervening layer 120*a, b*. A first of the plurality of piezoelectric films 110*a* is on a first side of the compressible intervening layer 120*a, b*, and a second of the plurality of piezoelectric films 110*b* is on a second side of the compressible intervening layer opposite the first piezoelectric film 110*a*.

When mechanical force 125 is applied to the first piezoelectric film 110*a*, the first piezoelectric film deforms towards the second piezoelectric film 110*b*. Because of the piezoelectric film 110*a* is formed from a piezoelectric material, the deformation of the film results in the generation of an electrical charge in the film. Similarly, when a mechanical force 125 is applied to both the first and second piezoelectric films 110*a, b* simultaneously, such as when the scaffold 100 is pinched between bones, the films deform towards each other.

In the embodiment shown, a third piezoelectric film 110*c* is provided in addition to the first two piezoelectric films 110*a, b*. The three piezoelectric films 110*a, b, c* are then arranged as substantially parallel planes with the third piezoelectric film 110*c* being between the first and second piezoelectric films 110*a, b*. In such an embodiment, the at least one compressible intervening layer 120*a, b* includes a first compressible intervening layer 120*a* between the first piezoelectric film 110*a* and the third piezoelectric film 110*c* and a second compressible intervening layer 120*b* between the second piezoelectric film 110*b* and the third piezoelectric film. As such, the three piezoelectric films 110*a, b, c* and the two compressible intervening layers 120*a, b* form a scaffold 100 taking the form of a sandwich.

The piezoelectric films 110*a, b, c* described and shown are typically biodegradable films, and the scaffold, and the related implant, does not include or require a battery. As such, all electrical signals output from the scaffold 100 during use are typically generated by the piezoelectric material of the films 110*a, b, c*.

Further, the embodiment shown and discussed herein typically includes two or three piezoelectric films 110*a, b, c*. In some embodiments, a single film may be formed from a piezoelectric material, and the remaining films are not piezoelectric. However, in typical embodiments, such as those discussed herein, at least the outer two films 110*a, b* are formed from piezoelectric materials.

Figure 3:
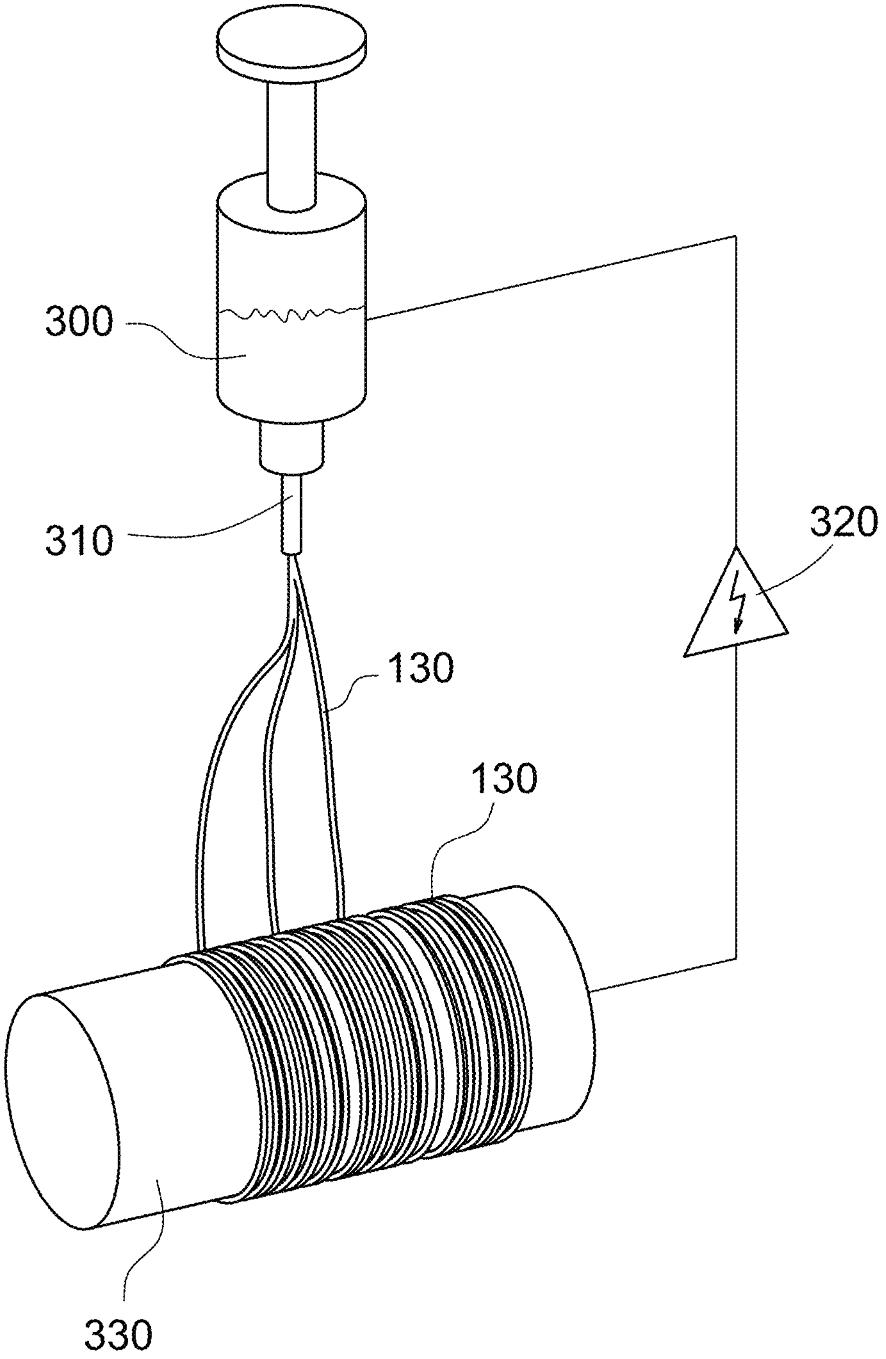
FIG. 3 is an image illustrating manufacturing steps involved in manufacturing the piezoelectric films 110*a, b, c*.

The piezoelectric films 110*a, b, c* may comprise poly (L-lactic acid) (PLLA), and may be manufactured using electrospinning techniques, as shown in the context of FIG. 3. Alternatively, in some embodiments, the piezoelectric films 110*a, b, c* may comprise silk, polyglycine, or collagen, and may be similarly manufactured by electrospinning.

FIG. 3 illustrates manufacturing steps involved in manufacturing the piezoelectric films 110*a, b, c*.

In manufacturing the piezoelectric films 110*a, b, c*, a solvent 300 is typically dispensed from a needle 310 in an electric field generated using a power source 320, to deposit nanofibers 130 onto a collector 330, such as a drum rotating at a speed sufficient so as to mechanically stretch and align the nanofibers. As such, for each individual piezoelectric film 110*a, b, c*, the nanofibers 130 are substantially aligned with each other, as shown in FIGS. 1 and 2.

The solvent 300 dispensed during the electrospinning process is typically PLLA, or whichever other material is to be used, dissolved in Dichloromethane (DCM) and molybdenum (MO) nanoparticles (NPs) may be suspended in Dimethylformamide (DMF) by means of sonication. In some cases, after the solvent 300 is mixed well, additional time, such as an hour, may be allowed for sonication in order to ensure that the MO NPs are well distributed in the mixture. While a specific embodiment is described, it is understood that other solvents may be used as well.

During dispensing of the solvent 300 from the needle 310, a high voltage, such as approximately 14 kV, is applied by a power source 320 between the needle and the collector 330. In the embodiment described, the collector is a drum 330, and the speed of the drum may be adjusted between 0 and approximately 4000 RPM to mechanically stretch and align the nanofibers 130. It is noted that the speed of the drum 330 during collection of the nanofibers 130 may relate directly to a level of piezoelectricity in the resulting piezoelectric film 110*a, b, c*. As such, a faster spinning drum 330, such as a drum spinning at 4000 RPM, will have fibers that are more aligned and which have a higher degree of piezoelectricity than a slower spinning drum.

Following the collection on the drum 330, the piezoelectric film 110*a, b, c* may be treated with annealing processes, which may be applied in stages at sequential temperatures. In some embodiments, a first annealing process may be applied at 110 degrees Celsius followed by a second annealing process at 160 degrees Celsius. Such an annealing process obtains high crystallinity and stabilizes the nanocomposites. In some embodiments, the annealing process may be followed by an additional stretching process.

The piezoelectric films 110*a, b, c* may be prepared having different MO content, typically in a range from 1%-30%. Further, the piezoelectric films 110*a, b, c* may have different thicknesses, but each film is typically between 15 and 25 μm thick.

The compressible intervening layers 120*a, b* are typically formed from hydrogels. In the embodiment shown, the layers 120*a, b* are a collagen hydrogel, and each layer is approximately 100-200 μm thick. In some embodiments, the collagen used in the compressible intervening layers 120*a, b* may be rat tail collagen. In some embodiments, the scaffold, taken as a whole, may be enclosed by collagen.

Because the nanofibers 130 are dispensed onto a spinning mechanical drum 330, the resulting films 110*a, b, c* comprise substantially aligned nanofibers 130, and each film has a first side 340 manufactured on a surface of the drum 330 and a second side 350 manufactured facing away from the drum and facing towards the needle 310. When compressed, the resulting films 110*a, b, c* each then have a first side 340 that generates a positive electrical charge and a second side 350 that generates a negative electrical charge. This is noted below in reference to FIG. 6. In the assembled scaffold 100, the first side 340 of the outer piezoelectric films 110*a, b* that generates a positive electric charge is typically arranged so as to face the adjacent compressible intervening layer 120*a, b*. Accordingly, the second side 350 of each of the outer films 110*a, b* that generate a negative charge comprises an outer surface of the scaffold 100, and faces outwards.

When manufactured by dispensing nanofibers 130 onto a drum 330, as discussed herein, the side of the film 110*a, b* facing the drum during manufacturing is typically the first side 340 and generates a positive electrical charge, and the side facing away from the drum is typically the second side 350 and generates a negative electrical charge. As such, the side manufactured facing the drum 330 typically faces the adjacent compressible intervening layer 120*a, b* when the piezoelectric film 110*a, b* is assembled into a scaffold 100.

In some embodiments, the piezoelectric films 110*a, b, c* may be manufactured using a different method, and may therefore not be collected on a drum 330. In such other manufacturing methods, a different surface may be determined to carry a negative electrical charge under compression.

In the assembled scaffold 100, because the nanofibers 130 are aligned, each film 110*a, b, c* has an orientation that can be defined by the nanofiber 130 direction. In some embodiments, the nanofibers 130 of the first and second piezoelectric films 110*a, b* may be parallel to each other while the intervening third piezoelectric film 110*c* is located between the first two and is arranged with its own substantially aligned nanofibers 130 substantially perpendicular with those of the first two.

Accordingly, the fiber directions of the first and the second layers 110*a, b* may be set parallel while the middle layer 110*c* was flipped upside down with the nanofiber oriented at an angle of 90° to the other 2 layers. This construct provides better mechanical properties due to the random, or offset, orientation of the films 110*a, b, c* in different layers when considering the entire scaffold, compared to other ways of stacking the sandwich structure. In this manner, the scaffold 100 may comprise the piezoelectric films 110*a, b, c* assembled into a porous sandwich scaffold.

Typically, as discussed elsewhere, a surface of the scaffold 100 designed to face a defect includes the second side 350 of the corresponding piezoelectric film 110_a_ facing outward. Accordingly, the second side 350 adjacent the defect then outputs a negative charge, and such negative charge is applied directly to the defect being treated. Further, in some embodiments, both the first and second piezoelectric films 110_a, b_ face the same direction, such that both are facing towards the defect. In such an embodiment, the second piezoelectric film 10_b_ is provided with its second side 350 facing towards the compressible intervening layer 120_b_ and the first side 340 then faces outwards. In such an embodiment, the third piezoelectric film 110_c_ mounted between the first two films 110_a, b_ may be upside down relative to the first and second films.

Figure 4:
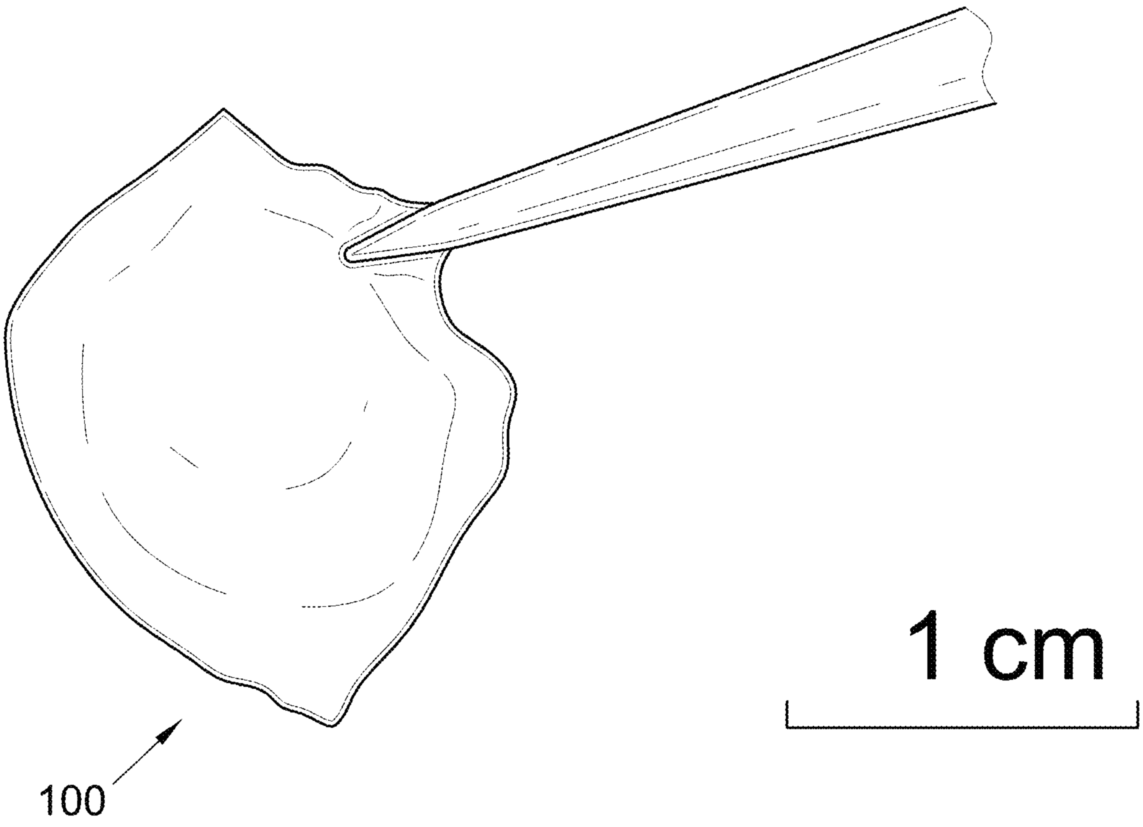
FIG. 4 is an image of the implantable scaffold of FIG. 1 fully assembled.

FIG. 4 is an image of the implantable scaffold 100 of FIG. 1 fully assembled. FIG. 5A is an image of the implantable scaffold 100 of FIG. 1 embedded in a user's knee 500. Figure SB is a scanning electron microscope (SEM) image of the implantable scaffold 100 adjacent an osteochondral defect 510.

As shown, the outer piezoelectric films 110_a, b_ may extend beyond the compressible intervening layers 120_a, b_ so as to fully enclose those layers. In some embodiments, an additional collagen layer may be applied to the outer surface of the scaffold 100, thereby finishing the implant. When implanted into a user's joint, in this case the user's knee 500, the scaffold 100 is located adjacent a cartilage or bone defect 510 to be treated. Such a defect 510 may be, for example, an osteochondral defect. When implanted, the second sFide 350 of the piezoelectric film 110_a_ adjacent the defect 510, that is the side that generates a negative electrical charge, typically faces the defect.

The scaffold 100, or an implant incorporating the scaffold, may be located within a pinch point or on a loadbearing surface 520 of the joint 500. As such, when the scaffold 100 is implanted into the user's knee 500, exercise performed by the user generates a mechanical force resulting in compression of the scaffold, such that the first piezoelectric film 110_a_ adjacent the defect 510 deforms towards the second piezoelectric film 110_b_ at the loadbearing surface 520.

Figure 6A:
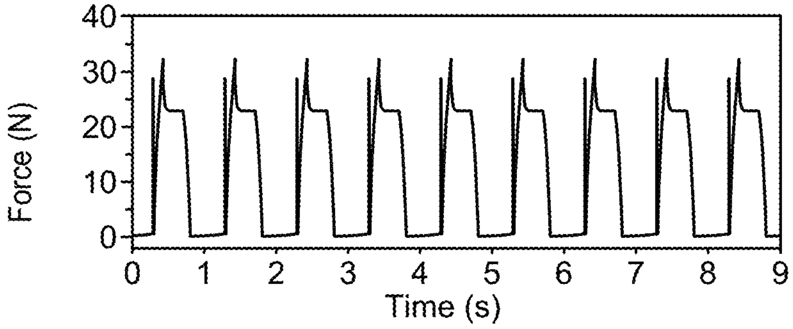
FIGS. 6A-C show an electric charge generated in a piezoelectric surface of the implantable scaffold of FIG. 1 when deformed under mechanical force.
Figure 6B:
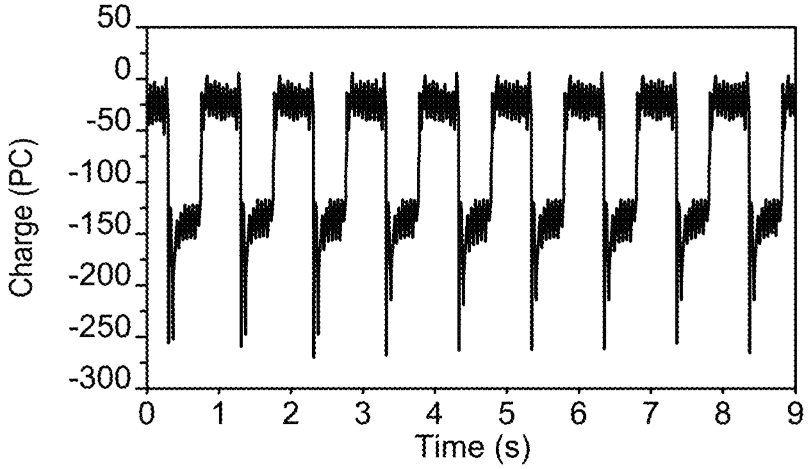
Figure 6C:
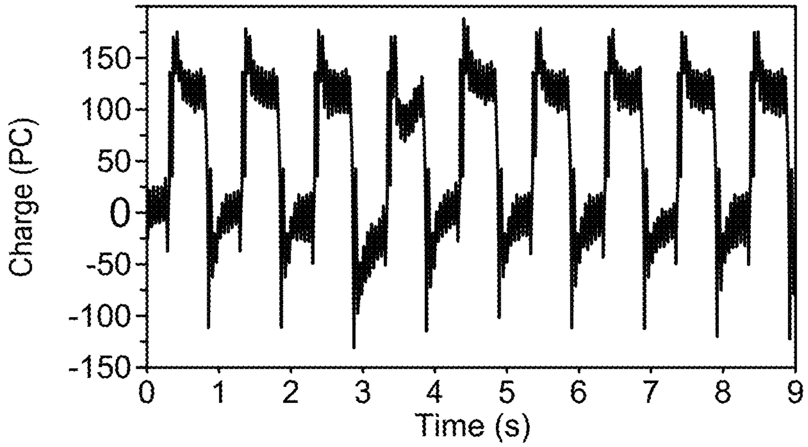

FIGS. 6A-C show an electric charge generated in a piezoelectric surface 340, 350 of the implantable scaffold 100 of FIG. 1 when deformed under mechanical force.

In order to demonstrate the electric charge generated under applied force, an actuator provides a compressive force of 30 N on the film 120_a_, as shown in FIG. 6A. The output charge of PLLA films was measured through an electrometer. As seen in the FIG. 6B, the top surface, referred to elsewhere herein as the second surface 350 (the surface closest to the electrospinning needle 310 during manufacturing) provides a negative charge, while as seen in FIG. 6C, the bottom surface, referred to elsewhere herein as the first surface 340 (the surface closest to the drum 330 during manufacturing) provides a positive charge, indicating the polarity of our processed piezoelectric films.

Figure 7:
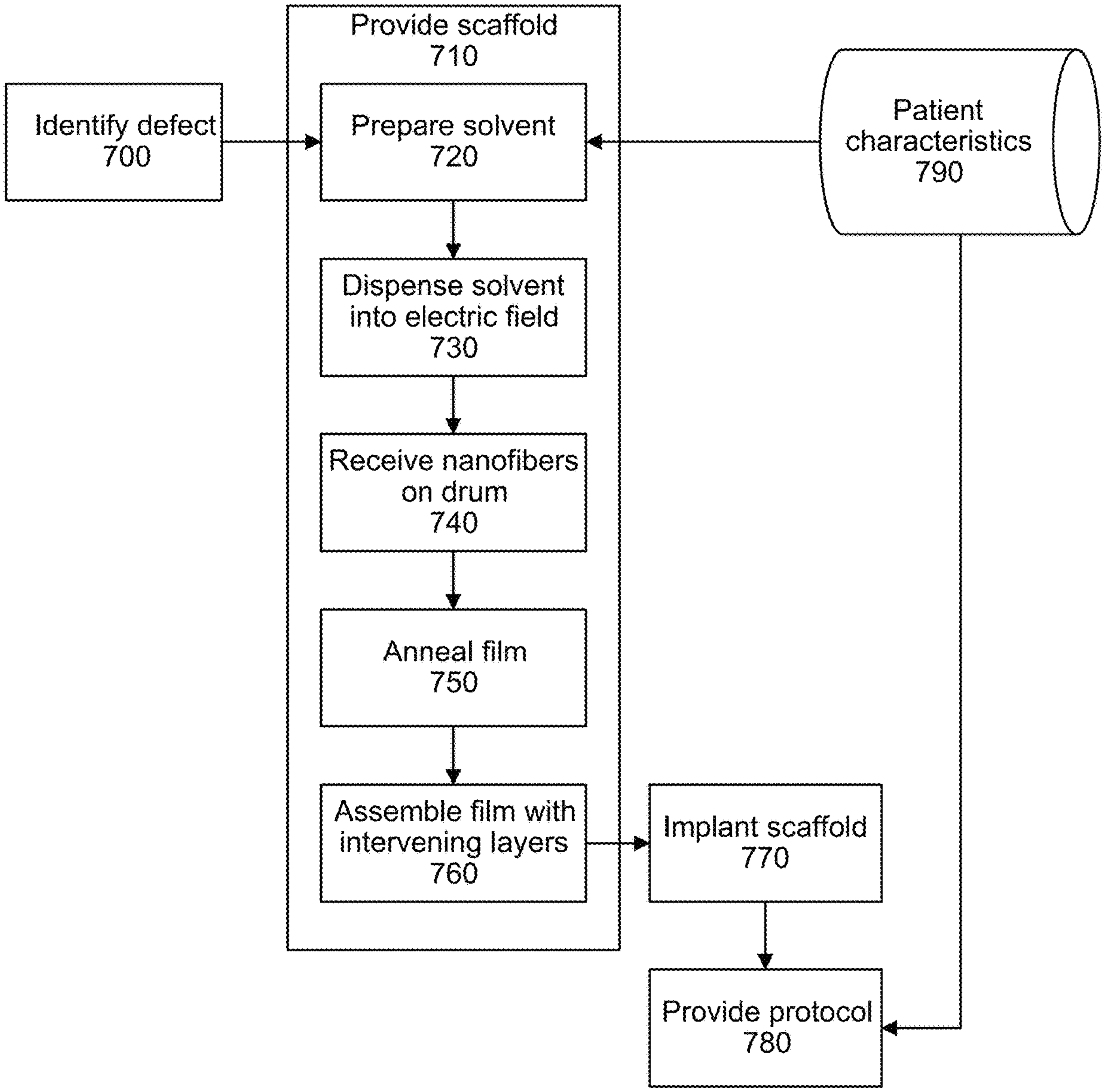
FIG. 7 is a flowchart illustrating a method of treating osteoarthritis using the scaffold of FIG. 1.

FIG. 7 is a flowchart illustrating a method of treating osteoarthritis using the scaffold 100 of FIG. 1. As shown, a method is provided for treating osteoarthritis and other diseases or injuries resulting in cartilage or bone defects that can be treated with electrostimulation.

The method involves first identifying (700) a cartilage or bone defect to be treated. Such a defect may be, for example, an osteochondral defect to be treated.

An implantable scaffold 100 is then provided (710) comprising a plurality of piezoelectric films 110_a, b, c_ and at least one compressible intervening layer 120_a, b_ between the piezoelectric films. Such a scaffold 100 may be that discussed above with respect to FIG. 1.

As part of the provision of the implantable scaffold 100 (at 710), the method may include the manufacturing of the scaffold prior to provision to the user. The piezoelectric films 110_a, b, c_ are typically manufactured by way of electrospinning. This may therefore include first preparing a solvent 300 (720) comprising poly (L-lactic acid) (PLLA) or, in some embodiments, silk, polyglycine, or collagen. The primary ingredient, such as PLLA, may then be dissolved in DCM, and MO NPs can be suspended in DMF using sonication, as discussed above.

The solvent 300 is then dispensed from a needle 310 (730) into an electric field and nanofibers 130 formed from the solvent are received at a collector drum 330 (740). Accordingly, the solvent 300 itself may form nanofibers 130 when exposed to the electric field, and such fibers may be collected at the drum 330. The collector drum 330 is rotated so as to mechanically stretch and align nanofibers 130 received from the solvent 300, resulting in piezoelectric films 110_a, b, c_ having substantially aligned nanofibers.

After the nanofibers 130 are received on the drum (at 740), thereby forming a piezoelectric film 110_a, b, c_, the film may be annealed (750). This may be in multiple stages at, for example, sequential temperatures of 110° C. and 160° C.

The piezoelectric films 110_a, b, c_ may then be combined (760) with the compressible intervening layers 120_a, b_ in order to form the scaffold 100 described above with respect to FIG. 1. As noted above, each of the piezoelectric films 110_a, b, c_ have a first side 340 that generates a positive charge and a second side 350 that generates a negative charge under compression. In the context of the scaffold, the first side 340 of each of the outer films 110_a, b_ is then assembled facing the adjacent compressible intervening layer 120_a, b_, and the second side 350 is then facing outward from the scaffold 100.

Once assembled, the implantable scaffold 100 is then implanted (770) adjacent the cartilage or bone defect 510 to be treated, which may be an osteochondral defect. The scaffold 100 is typically implanted within a pinch point or at a load bearing surface 720 of a joint 500. This is shown, for example, in FIG. 5. Because the scaffold 100 is assembled with the second side 350 of the outer piezoelectric film 110_a_, which generates a negative electric charge, facing outward, the second side of the corresponding film faces the cartilage or bone defect 510 to be treated.

The user in whom the scaffold has been implanted is then provided with an exercise protocol (780) for generating periodic impact at the pinch point of the joint 500. The exercise protocol is designed such that the periodic impact applies a mechanical force to a first piezoelectric film 110_a_ of the plurality of piezoelectric films 110_a, b, c_ of the scaffold 100, such that the first film 110_a_ compresses the compressible intervening layer 120_a, b_ and deforms towards the second film 110_b_.

As noted above, the scaffold 100 described herein is typically biodegradable and is not provided with a battery. As such, following implant of the scaffold 100, performance of the exercise protocol will lead to the generation of an electrical charge at the scaffold. Over time, the scaffold 100 will degrade. However, because no battery is implanted, the scaffold 100 can safely remain in place until fully biodegraded, even after it can no longer generate electricity.

In the embodiment shown in FIG. 5, the cartilage or bone defect 510 is an osteochondral defect, and such defect is in a user's knee joint 500. As such, the exercise protocol provided (at 780) may be a walking protocol for generating a periodic impact at the knee joint. Such periodic impact then applies a mechanical force 125 and compresses the scaffold 100, thereby generating an electrical charge at the surface of the scaffold 100, which is in turn adjacent the defect 510.

In some embodiments, upon identifying the defect 510 to be treated (at 700), and prior to providing the scaffold (at 710), at least one characteristic of the implantable scaffold 100 is selected based on a characteristic of the user, or patient, in which the defect was identified 790. Such patient characteristics 790 may be retrieved from a database when needed, and may be considered at the beginning of the scaffold manufacturing or provision process.

As an example, in some embodiments, a porosity of nanofibers of the plurality of piezoelectric films 110*a, b, c* may be selected based on a characteristic of the patient. For example, such a characteristic may be selected based on a weight of the patient. Similarly, a number of compressible layers 120*a, b* may be selected based on a characteristic of the patient 790. While the embodiment shown herein provides a scaffold 100 having three layers of piezoelectric films 110*a, b, c* and two compressible intervening layers 120*a, b*, the scaffold may instead be provided with additional piezoelectric layers, such as 4 or 5 layers, with compressible intervening layers separating all such layers. Alternatively, a scaffold 100 may be provided with only two piezoelectric layers 110*a, b* and only a single compressible intervening layer 120*a*.

Similarly, a thickness of the compressible intervening layers 110*a, b* may be selected based on a characteristic of the patient 790 such as patient weight. Other characteristics may be considered as well. For example, patient fitness may be considered in selecting characteristics for the scaffold 100. Similarly, patient characteristics 790 may be considered in defining an exercise protocol to be provided to the patient after implantation. For example, if a patient is expected to be sufficiently fit to jog, rather than walk, a scaffold may be manufactured on such a basis and tuned for a level of impact associated with jogging, rather than walking. Similarly, the protocol provided may specify jogging rather than walking, and a pace for the patient may be selected on that basis.

In evaluating the results of using the applied force to enhance chondrogenesis of cultured stem cells in vitro, Adipose-Derived Stem Cells (Rabbit ADSC) were considered, as the autologous ADSCs can be easily harvested from the subcutaneous fat tissues of patients and easily expanded in vitro for potential future use in combination (if needed) with the piezoelectric scaffold 100 described herein to further enhance the chondrogenesis. The piezoelectric PLLA films 110*a, b, c*, along with their nonpiezoelectric counterparts for comparison, were fabricated to a porous sandwich scaffold 100 together with rat tail collagen used as the compressible intervening layers.

The scaffold 100 considered had three layers of PLLA nanofiber films 110*a, b, c* each of which has aligned nanofiber 130. The fiber directions of the first layer 110*a* and the third layer 110*b* were set parallel while the middle layer 110*c* was flipped upside down with the nanofiber oriented at an angle of 90° to the other 2 layers. This construct provides better mechanical properties due to the random orientation of the films 110*a, b, c* in different layers when considering the entire scaffold 100, compared to other ways of stacking the sandwich structure. A customized actuation system was then used to induce a controllable applied impact pressure (0.08 MPa) for 14 days and 20 min/day, on the scaffold with ADSC cultured on the negative surface 350 of the scaffold 100 (i.e. the surface generating negative charge under applied force as seen in FIG. 6B).

Figure 8A:
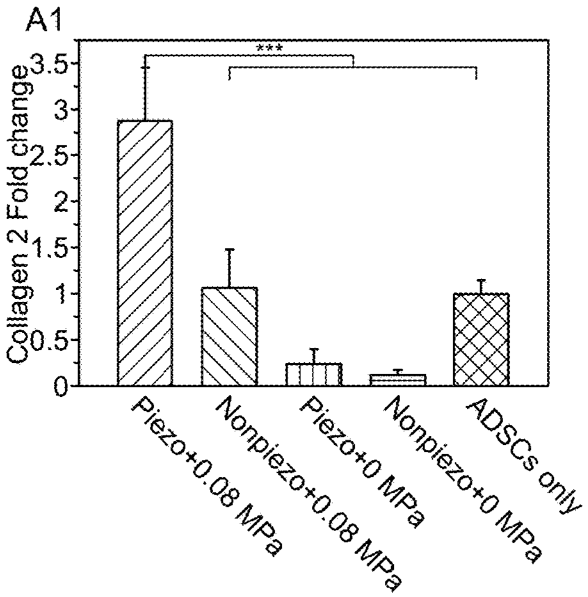
FIGS. 8A-C show the expression of chondrogenic genes with and without applied pressure.
Figure 8B:
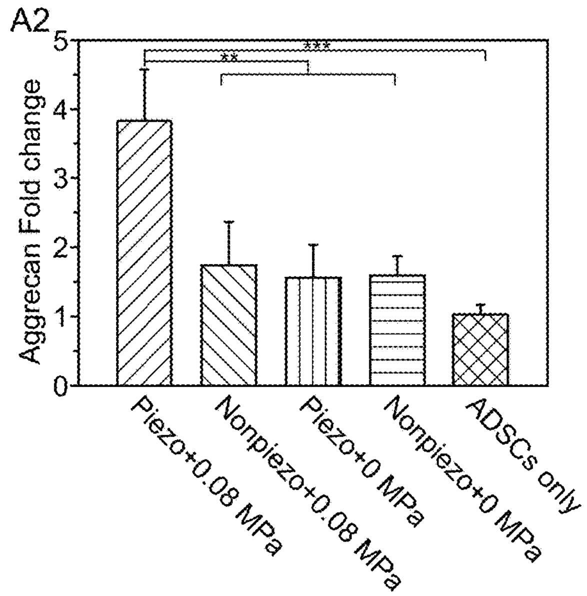
Figure 8C:
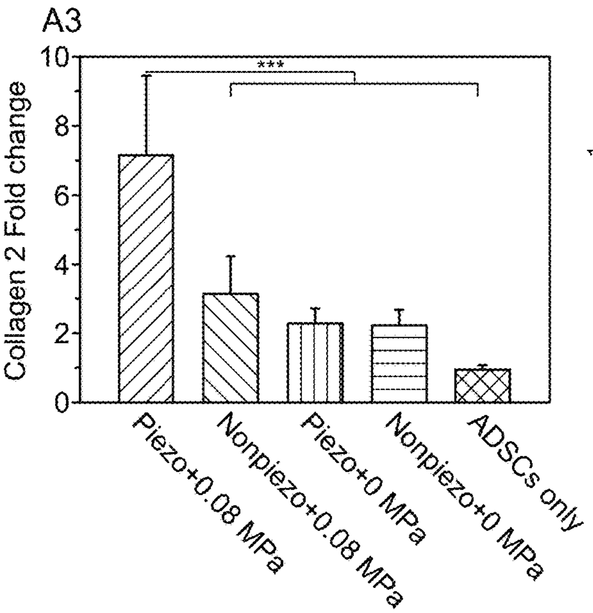
Figure 8D:
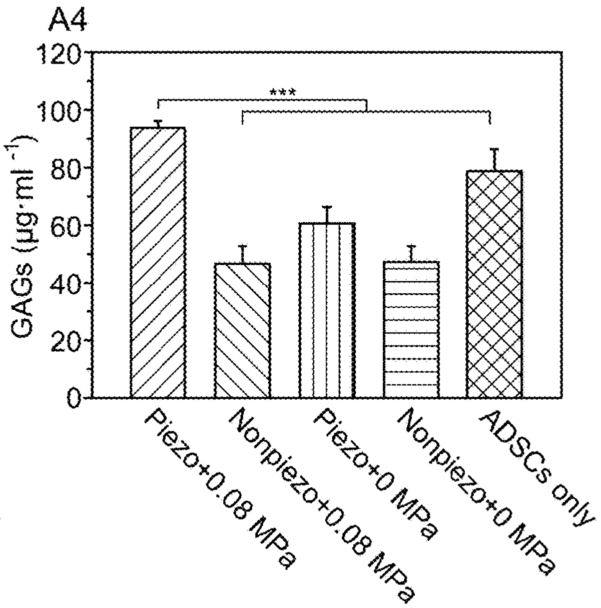
FIG. 8D shows Glycosaminoglycans (GAGs) content in trials.
Figure 9A:
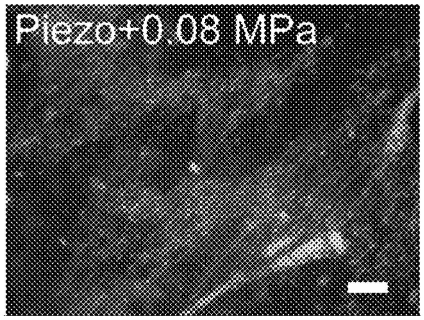
FIGS. 9A-D show the results of immunofluorescence collagen staining.
Figure 9B:
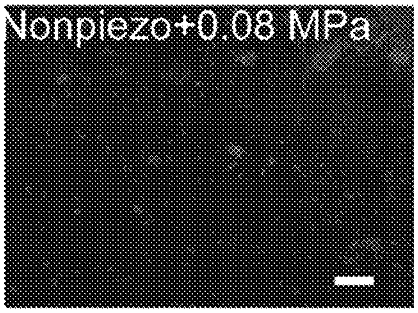
Figure 9C:
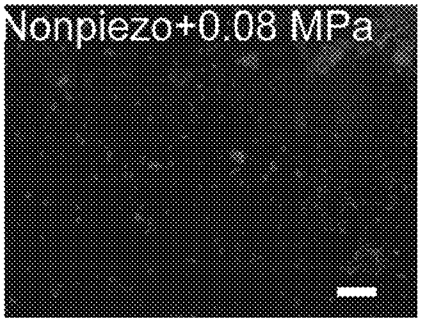
Figure 9D:
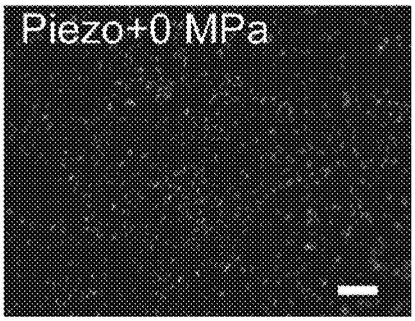
Figure 10A:
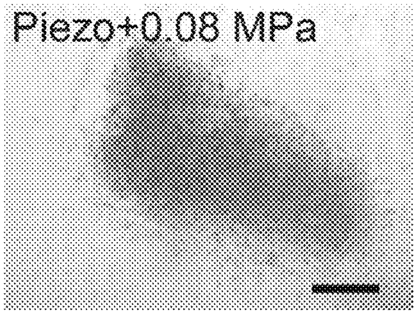
FIGS. 10A-D show the results of Alcian Blue staining.
Figure 10B:
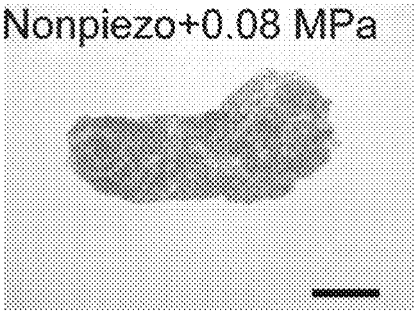
Figure 10C:
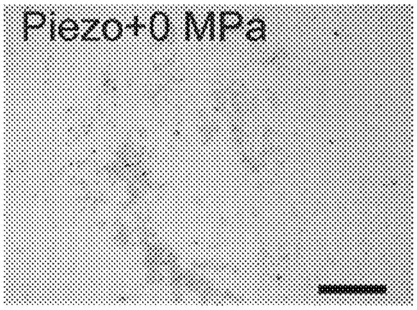
Figure 10D:
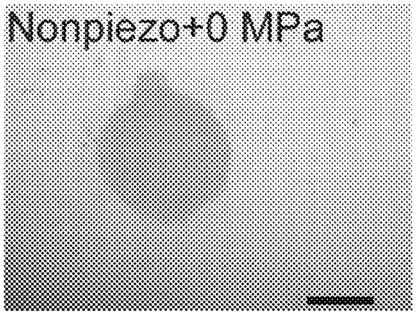

FIGS. 8A-C show the expression of chondrogenic genes with and without applied pressure. FIG. 8D shows Glycosaminoglycans (GAGs) content for each trial.

The negative surface 350 was selected, as negative charges tend to promote chondrogenesis better than positive charges. For the in vitro experiments, a chondrogenic medium was used, containing TGF-β3, Dexamethasone, sodium pyruvate, ascorbic acid 2-phosphate to promote chondrogenic differentiation of the stem cells. The expression of related genes, including type II Collagen, Aggrecan and Sox-9, as well as glycosaminoglycans (GAGs) content are shown in FIG. 8A-D. Clearly, there is a significant improved expression of type II collagen, as shown in FIG. 8A, Aggrecan, as shown in FIG. 8B, and Sox-9, as shown in FIG. 8C, in the piezoelectric scaffold 100 with applied 0.08-MPa of force (i.e., Piezo+0.08 MPa), compared to either piezoelectric scaffold without application of force (i.e. Piezo+0 MPa), or nonpiezoelectric scaffold with or without the application of such force.

As shown in FIGS. 9A-D, Immunofluorescence (IF) collagen type II staining was conducted, and as shown in FIGS. 10A-D. Alcian Blue staining was further conducted to confirm the effect of piezoelectric stimulation on the chondrogenic differentiation of the stem cells. Indeed, as shown in the FIGS. 9A-D and 10A-D, ADSCs cultured directly on the piezoelectric scaffold 100 with the applied force presented a much higher expression of collagen type II than any other groups. Similar results were seen through Alcian Blue staining. These data clearly indicate that the piezoelectric charge, only generated when combining the piezoelectric PLLA scaffold with applied force, is the driving force for the enhanced chondrogenesis.

Figure 11A:
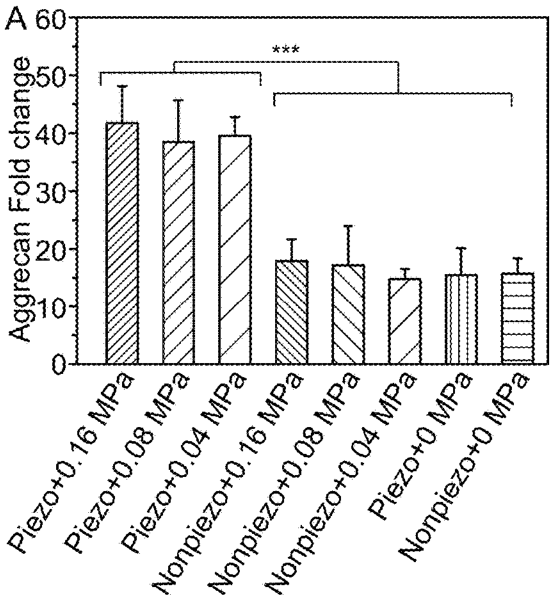
FIGS. 11A-C show the results of different pressure applications.
Figure 11B:
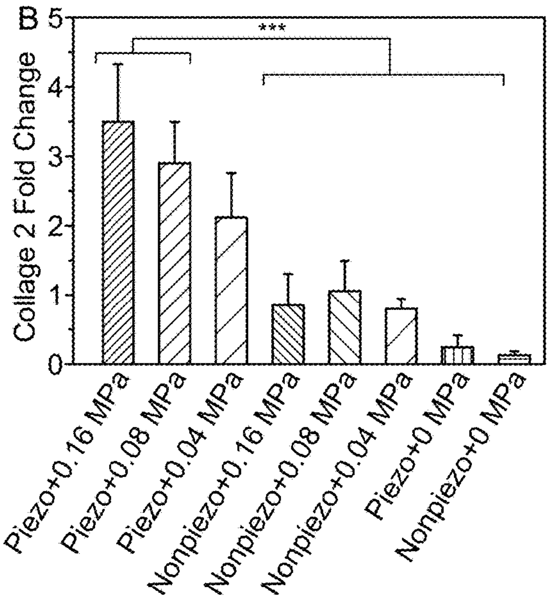
Figure 11C:
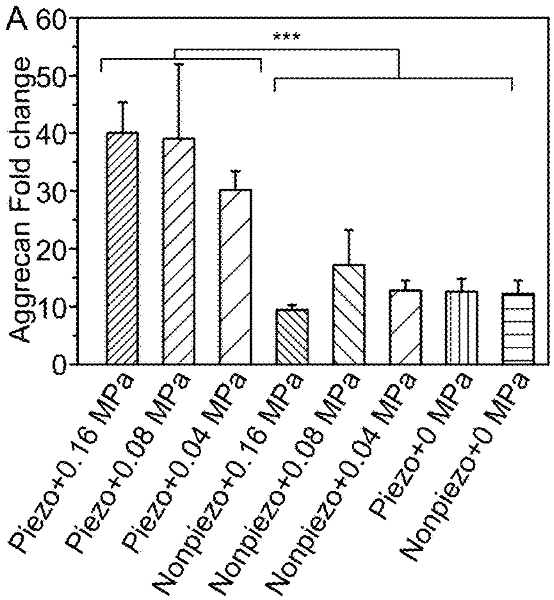

Besides electrical charges, mechanical forces or joint loads may influence the chondrogenesis and cartilage healing. As such, a similar assessment to that discussed above with respect to FIGS. 8A-D was considered at different levels applied pressure. FIGS. 11A-C show the results of different pressure applications. ADSCs were again cultured on the piezoelectric PLLA scaffold 100 in the same culture condition as in FIGS. 8A-D, but with other applied pressure of 0.04 MPa and 0.16 MPa. Although there seems to be more sulfated GAGs deposition in the piezoelectric scaffold 100 groups with 0.04 MPa and 0.16 MPa, the piezoelectric scaffold groups with 0.04 MPa or 0.16 MPa showed a similar chondrogenic expression of aggrecan (FIG. 11A), collagen type II (FIG. 11B) and Sox-9 (FIG. 11C), compared to the piezoelectric scaffold group with 0.08 MPa after 14-day culture of the ADSCs on the piezoelectric scaffold.

Figure 12:
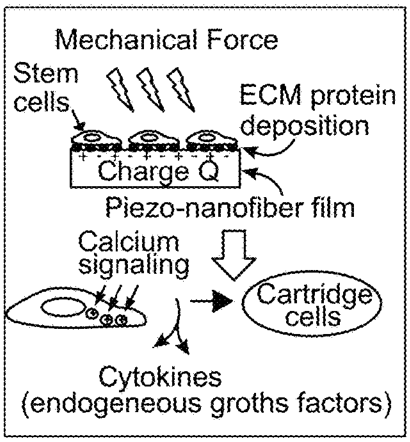
FIG. 12 illustrates a mechanism believed to promote chondrogenic differentiation.

FIG. 12 illustrates a mechanism believed to promote chondrogenic differentiation. It is believed that the surface charge, generated on the piezoelectric PLLA scaffold 100, can attract the extracellular matrix (ECM) protein to promote cell adhesion and at the same time, trigger the Ca2+ influx via voltage-gated ion channels. This then leads to the cellular secretion of endogenous growth factor (e.g., TGF-β1) beneficial to chondrogenic differentiation. To support this understanding, several biochemical assays were prepared to quantify the protein (e.g., fibronectin) attracted by the charged surface, the secreted endogenous TGF-β1 protein, and the chondrogenic-gene expression with and without the presence of Ca2+ inhibitor.

Figure 13A:
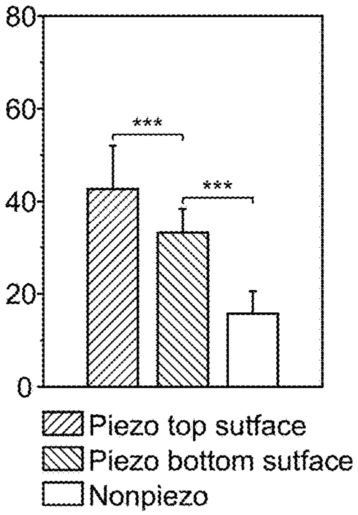
FIG. 13A illustrates Fibronectin adsorption on the surface of the piezoelectric PLLA film with applied pressure of 0.08 MPa.

For the protein attraction test, fibronectin was used as an ECM protein model because fibronectin is abundant in blood clots which often acts as the first phase of the tissue healing process. Piezoelectric film was found to attract more protein when compared with the nonpiezoelectric film (FIG. 13A) ($p<0.001$). Specifically, the top surface of piezoelectric film, which has net negative (−) charges under force, showed a higher ability to absorb protein compare with the bottom surface with net positive (+) charges ($p<0.001$).

For the secretion of endogenous growth factor, the release of TGF-β1 from the ADSCs was assessed. The growth-promoting factor, TGF-β1, is known for its role in chondrogenic differentiation of stem cells and often serves as the essential component in a chondrogenic medium in vitro. Electrical stimulation (ES) may induce the chondrogenesis of stem cells even in the absence of TGF-β in the culture medium, due to the ability of the ES to induce the cells for a self-secretion of endogenous TGF-β and/or the activation of TGF-β signaling pathway. The same effect might happen in piezoelectric stimulation. To show such an effect, the TGF-β3 amount in the chondrogenic medium for the cell culture process was reduced and chondrogenic outcomes from the stem cells stimulated by the piezoelectric scaffold 100 were assessed with applied pressure (0.08 MPa).

Figure 13B:
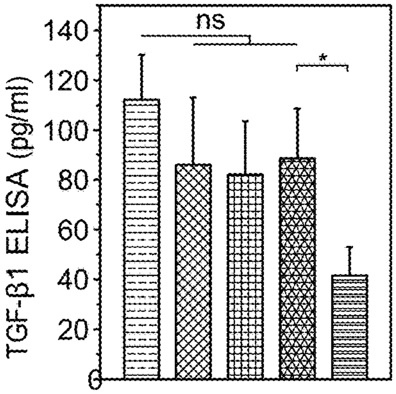
FIG. 13B illustrates the concentration of endogenous cytokine of TGF-β1 inside the supernatant after 3 days of culturing ADSCs on the PLLA films with applied pressure of 0.08 MPa under different culture conditions of varying exogenous TGF-β3 concentration.
Figure 13C:
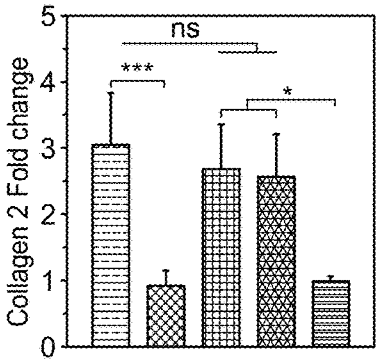
FIGS. 13C-E illustrate expression of chondrogenic genes (Collagen type II, Aggrecan and SOX-9) after 14 days culture of ADSCs under the piezoelectric stimulation with different concentrations of exogenous TGF-β3 in the culture medium.
Figure 13D:
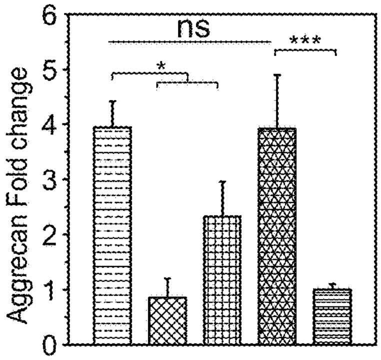
Figure 13E:
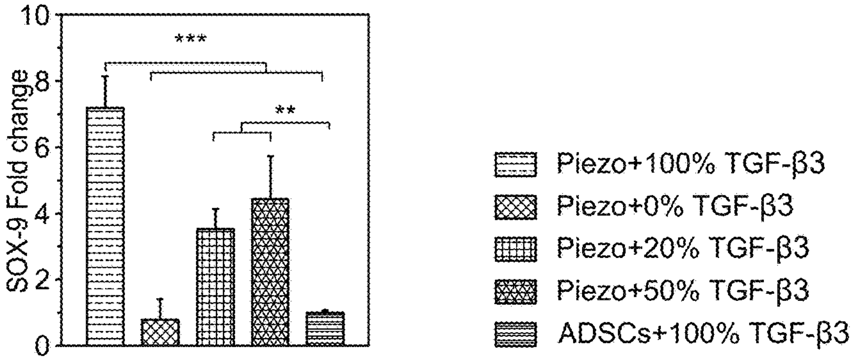

The supernatant of the culture media was collected and an Enzyme-linked immunosorbent assay (ELISA) was implemented (as shown in FIG. 13B) to specifically assess the TGF-1 protein secreted by the cells. The results revealed an increased content of TGF-β1 for all the groups with piezoelectric scaffolds 100, regardless of how much exogenous TGF-β3 existed in each culture medium. We further conducted PCR to assess the gene expression of cells cultured with a reduced amount of exogenous TGF-β in the culture medium. As seen in FIG. 13C, no significant difference appears for collagen type 2 expression when exogenous TGF-β3 is reduced to 50% and 20%. There was also no significant difference for aggrecan expression at 50% TGF-β3, compared with piezoelectric stimulation at 100% TGF-β3 supplemented chondrogenic medium. However, down-regulated expression of aggrecans was found when the TGF-β3 is less than 20%, as seen in FIG. 13D. As seen in FIG. 13E, Sox-9 expression were reduced after culturing in all TGF-β3 free media. Thus, while some level of exogenous TGF-β3 is still required (>20%) to induce chondrogenic differentiation of the stem cells in vitro, the results suggest that the piezoelectric charge might have a considerable effect on stimulating the secretion of endogenous TGF-β1 factor to enhance the chondrogenic differentiation of the ADSC stem cells conditioned with a low amount of exogenous TGF-β3.

To test the effect of calcium signaling on chondrogenesis, Verapamil was used, which is known as a voltage-gated calcium channel (VGCC) inhibitor to prevent the intracellular influx of Ca2+42. To test if the VGCC plays a role in chondrogenesis during the piezoelectric stimulation, Verapamil was introduced into the culture media. As seen in FIGS. 14A-C, the addition of Verapamil decreased the expression of collagen type II, aggrecan and SOX-9 in the piezoelectric stimulation group (i.e. the group of piezo+ force). These results imply that piezoelectric charges stimulate chondrogenesis via the opening of VGCC to facilitate the influx of Ca2+.

After showing that the piezoelectric scaffold 100 with applied force could promote chondrogenesis in vitro, similar results are demonstrated in vivo to demonstrate the effect of the piezoelectric scaffold implanted in rabbit knee joints with exercise-induced joint-motion to promote a significant cartilage healing in vivo. Rabbits were provided with critical-sized osteochondral (OC) defects (~4 mm in diameter and 2 mm in depth) and the scaffold 100 was implanted into the defects. The rabbits were then trained on treadmills to induce joint loads on the implanted scaffolds. Using the collected videos on the rabbit motion with tracking-markers and applying kinematic modeling, the applied joint load was estimated as pressure in the range of 70 kPa to 600 kPa during the rabbit's hopping, corresponding to a specific treadmill training (1 Hz of hopping at 1 mph of the treadmill speed for rabbits with an average body mass of 3.5 kg). This pressure range includes the applied pressure value of 80 kPa which is beneficial for chondrogenesis in the in vitro assessment, thus indicating that the training should provide a reasonable range of joint loads to promote cartilage healing.

TABLE 1

Lower and Upper Bound Estimates for Rabbit Knee Joint Loading

| | Lower Estimate | Upper Estimate |
|---|---|---|
| Cross-Sectional Area | 100 $mm^2$ | 400 $mm^2$ |
| Knee Joint Loading | 1 × Body Weight | 2.1 × Body Weight |
| Pressure on Knee | 70 kPa | 600 kPa |

Note:
Mass of Rabbit: 3.5 kg
Walk Rate: 1 Hz

Prior to treadmill training, the animals were preconditioned to use the treadmill before surgery. After the implantation-surgery, rabbits were allowed a one-month rest as a relief time. One month was chosen for the relief time, as a shorter time period than that is believed to cause more damage than beneficial healing. The regenerative outcome at the endpoints of two-months (i.e. one-month exercise) and three months (i.e. two-month exercise) post implantation surgery was then evaluated.

Figure 15:
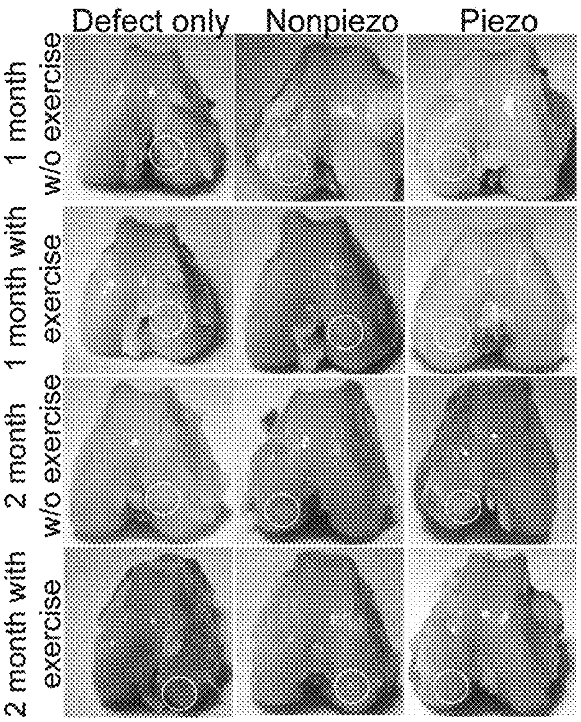
FIG. 15 illustrates cartilage tissue from variations of the trials described herein.

As shown in FIG. 15, less regeneration was observed in the sham/control groups of non-piezo, scaffolds with and without exercise, compared to the experimental group of piezoelectric scaffolds with exercise (i.e. piezo.+exercise). Also, the OC defects were only partially filled with new cartilage and bone in the control/sham groups. In contrast, the (piezo.+exercise) group shows much improved regeneration with the entire OC defects virtually filled with neocartilage tissues. We found a smoother surface and better integration with the surrounding host cartilage in this group of (piezo.+exercise), compared to the other control/sham groups. In particular, the repaired tissue showed a glossy white color after two months of exercise, which was similar to native cartilage.

Figure 16:
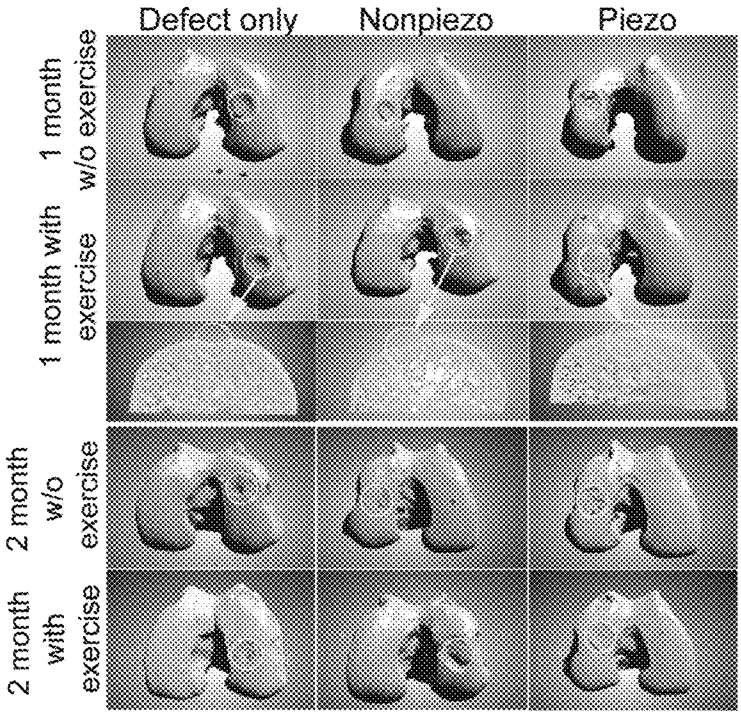
FIG. 16 illustrates micro-CT reconstructions of the subchondral bone in the trials of FIG. 15.
Figure 17:
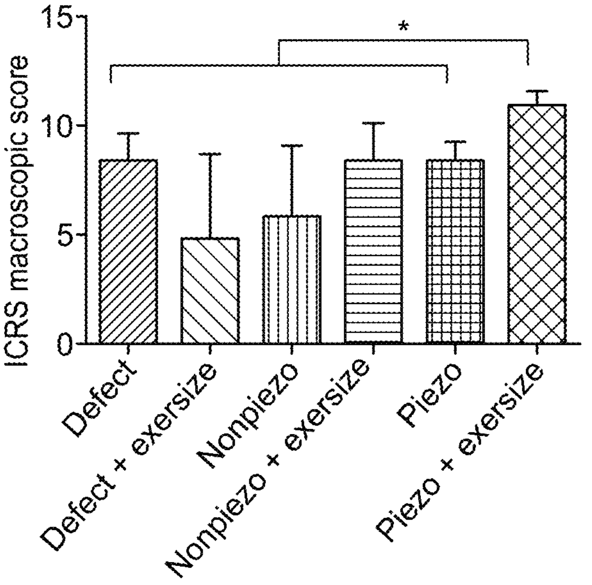
FIG. 17 illustrates ICRS macroscopic cartilage evaluations scores.
Figure 18:
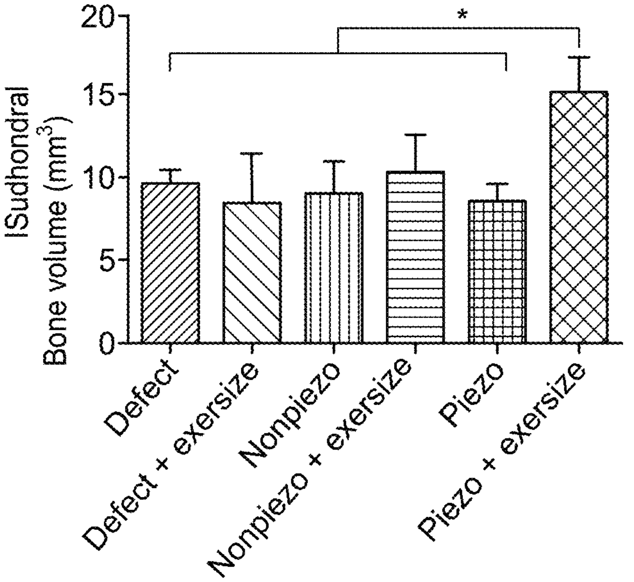
FIG. 18 illustrates micro-CT derived subchondral bone volume.
Figure 19A:
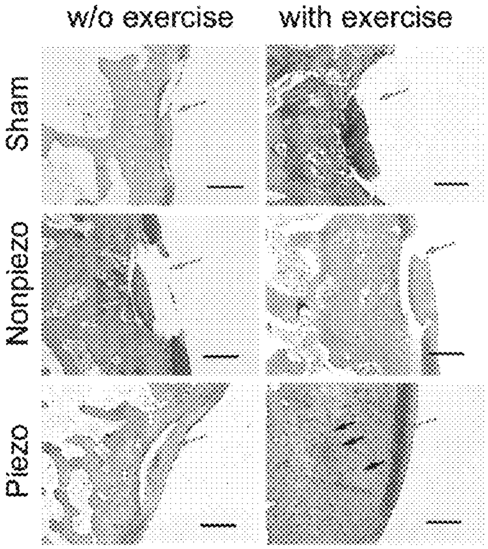
FIGS. 19A-C illustrate histology images comparing variations of the trials described herein.
Figure 19B:
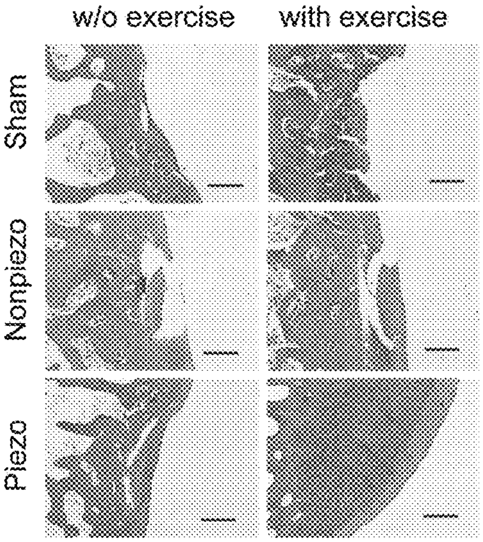
Figure 19C:
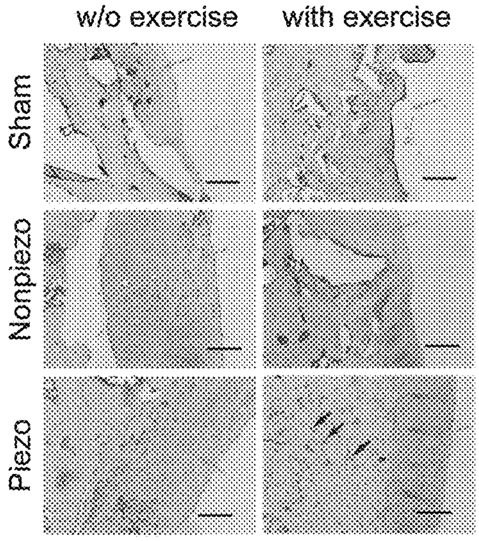
Figure 19D:
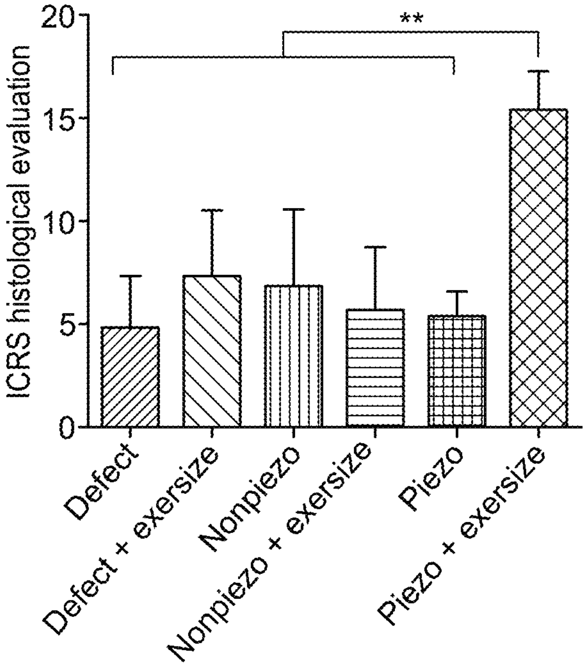
FIG. 19D provides an ICRS histological evaluation score.
Figure 20A:
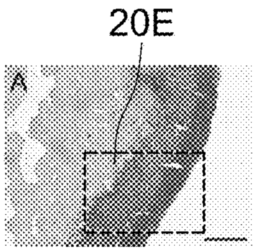
FIGS. 20A-D illustrate regenerated defects in four rabbits.
Figure 20B:
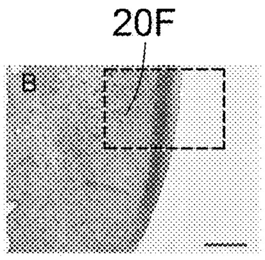
Figure 20C:
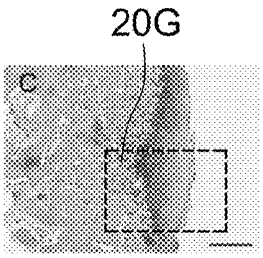
Figure 20D:
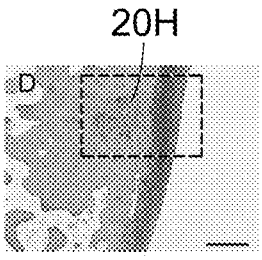
Figure 20E:
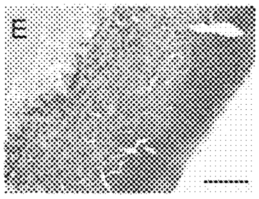
FIGS. 20E-H illustrate cell arrangements of highlighted areas in FIGS. 20A-D respectively.
Figure 20F:
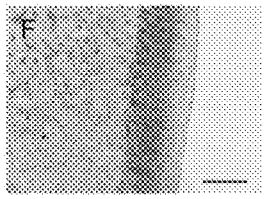
Figure 20G:
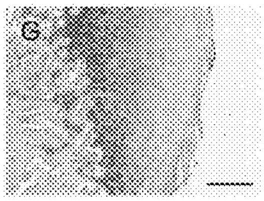
Figure 20H:
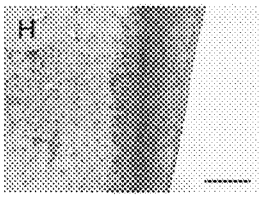

FIG. 16 shows results of micro-CT reconstruction used to assess the subchondral bone regeneration. As shown, the 3D micro-CT reconstruction revealed an improved subchondral bone regeneration, consistent with that shown in FIG. 15 for the (piezo.+exercise) group in comparison with the other sham/control groups at each time point. Per the gross observations, the ICRS macroscopic evaluation score, as shown in FIG. 17, showed that the repaired cartilage was markedly better for the (piezo.+exercise) group compared with all the other control/sham groups. Meanwhile, following FIG. 16, the micro-CT derived subchondral bone volume, shown in FIG. 18, demonstrated a higher amount of bone regeneration in the (piezo.+exercise) group. This corresponds with previous observations that the piezoelectric stimulation can regenerate calvarial bone defects in mice.

Examining the histological staining based on H&E, Safranin O, and Immune-histochemical (IHC) staining of collagen II, presented outstanding evidence of hyaline cartilage regeneration in the femoral condyle OC defects, as seen in FIGS. 19A-D. This evidence corresponds to the results illustrated above in FIG. 15, in which the non-exercise or non-piezo, scaffold groups only show partially filled defects, as shown in histology images in FIG. 19A-C. This is in conjunction with evidence of loose fibrotic neocartilage tissues with a disordered structure and limited regenerated effect in the OC defects for these control/sham groups. In contrast, the (piezo, scaffold+exercise) group showed a superior cartilage regeneration with a clear and typical chondrocyte shape at the superficial layer of the hyaline cartilage. Without exercise, the piezoelectric scaffold also exhibits some improved cartilage regeneration, most likely due to the free or passive movements of the rabbits (without the active treadmill training), which can also activate the piezoelectric scaffold to some degree.

The piezo scaffold+exercise group still shows the best regeneration with an entire OC defect filled with neocartilage tissues and a clear healthy hyaline cartilage structure shown in the histology staining, similar to surrounding native cartilage, as visible in FIGS. 19A-C and FIGS. 20A-H. In FIGS. 20A-H, it is noted that FIGS. 20A-D illustrate the regenerated defects in four different rabbits, while FIGS. 20E-H show the cell arrangement in the highlighted area of FIGS. 20A-D respectively. Massive Safranin O positive chondrocytes with high content of proteoglycans are evident in each sample. The scale bars for FIGS. 20A-D are 500 μm, and the scale bar for FIGS. 20E-H are 200 μm.

The notable finding is that, for the piezo scaffold+exercise group, the regenerated defect demonstrates massive Safranin O positive (black arrows in FIG. 19A) chondrocytes with high content of proteoglycans. This is in accordance with the IHC collagen II staining (black arrows in FIG. 19C), where the chondrocytes within the regenerated defect showed high expression of collagen type II (i.e. the presence of hyaline cartilage). This unique phenomenon may be attributed to the fact that the piezoelectric stimulation under exercise generates charges (negative surface faced into the subchondral bone). These charges initially attracted ECM proteins (supported by an experiment in FIG. 13A), and subsequently attracted the stem cells/chondrocytes. The latter migrated into the defect/scaffold location from the bone marrow deep inside the subchondral bone. The presence of chondrocytes and collagen II expression inside the subchondral bone might be remnants of that migration in the piezoelectric stimulation groups.

The methods according to the present disclosure may be implemented on a computer as a computer implemented method, or in dedicated hardware, or in a combination of both. Executable code for a method according to the present disclosure may be stored on a computer program product. Examples of computer program products include memory devices, optical storage devices, integrated circuits, servers, online software, etc. Preferably, the computer program product may include non-transitory program code stored on a computer readable medium for performing a method according to the present disclosure when said program product is executed on a computer. In an embodiment, the computer program may include computer program code adapted to perform all the steps of a method according to the present disclosure when the computer program is run on a computer. The computer program may be embodied on a computer readable medium.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions. Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. An implantable scaffold comprising:

a plurality of piezoelectric films; and at least one compressible intervening layer, wherein a first of the plurality of piezoelectric films is on a first side of the compressible intervening layer and a second of the plurality of piezoelectric films is on a second side of the compressible intervening layer opposite the first piezoelectric film, wherein upon applying a mechanical force to the first piezoelectric film, the first piezoelectric film deforms towards the second piezoelectric film, wherein the plurality of piezoelectric films are biodegradable and wherein the implantable scaffold does not comprise a battery, wherein each of the plurality of piezoelectric films comprise at least one of poly (L-lactic acid) (PLLA), silk, polyglycine, or collagen, and wherein each of the plurality of piezoelectric films are manufactured by electrospinning, wherein the plurality of piezoelectric films are manufactured by dispensing a solvent from a needle in an electric field to deposit nanofibers onto a drum rotating at a speed sufficient so as to mechanically stretch and align the nanofibers, wherein each of the plurality of piezoelectric films comprises nanofibers substantially aligned with each other, wherein the plurality of piezoelectric films is three piezoelectric films arranged as substantially parallel planes with the third piezoelectric film being between the first and second piezoelectric films, and wherein the at least one compressible intervening layer is a first compressible intervening layer between the first piezoelectric film and the third piezoelectric film and a second compressible intervening layer between the second piezoelectric film and the third piezoelectric film, and wherein the substantially aligned nanofibers of the first piezoelectric film are substantially parallel with the substantially aligned nanofibers of the second piezoelectric film and are substantially perpendicular with the substantially aligned nanofibers of the third piezoelectric film.

2. The implantable scaffold of claim 1 wherein each of the piezoelectric films has a first side manufactured on a surface of the drum and a second side manufactured facing away from the drum, and wherein the first side of each of the piezoelectric films faces the compressible intervening layer.

3. The implantable scaffold of claim 1 wherein each of the piezoelectric films has a first side for generating a positive electrical charge and a second side for generating a negative electrical charge, and wherein the first side of each of the piezoelectric films faces the compressible intervening layer.

4. The implantable scaffold of claim 1 wherein the compressible intervening layer is a hydrogel.

5. A method of treatment for osteoarthritis comprising:

identifying a cartilage or bone defect to be treated;

providing an implantable scaffold comprising a plurality of piezoelectric films and at least one compressible intervening layer between at least two of the plurality of piezoelectric films;

implanting the implantable scaffold adjacent the cartilage or bone defect to be treated and within a pinch point of a joint; and providing an exercise protocol for generating periodic impact at the pinch point, such that the periodic impact applies a mechanical force to a first piezoelectric film of the plurality of piezoelectric films such that the first piezoelectric film compresses the compressible intervening layer and deforms towards the second piezoelectric film, wherein the cartilage or bone defect to be treated is in a knee joint and wherein the exercise protocol is a walking protocol for generating periodic impact at the knee joint.

6. The method of claim 5 wherein each of the piezoelectric films has a first side for generating a positive electrical charge and a second side for generating a negative electrical charge, and wherein after implanting the implantable scaffold, the second side of the first piezoelectric film faces the cartilage or bone defect to be treated.

7. The method of claim 5 wherein the plurality of piezoelectric films are biodegradable and wherein no battery is implanted with the implantable scaffold.

8. The method of claim 7 wherein each of the plurality of piezoelectric films comprise at least one of poly (L-lactic acid) (PLLA), silk, polyglycine, or collagen, and wherein each of the plurality of piezoelectric films are manufactured by dispensing a solvent from a needle in an electric field to deposit nanofibers on a surface, and wherein the nanofibers of each of the plurality of piezoelectric films are substantially aligned.

9. The method of claim 8 wherein the plurality of piezoelectric films is three piezoelectric films arranged as substantially parallel planes with the third piezoelectric film being between the first and second piezoelectric films, and wherein the at least one compressible intervening layer is a first compressible intervening layer between the first piezoelectric film and the third piezoelectric film and a second compressible intervening layer between the second piezoelectric film and the third piezoelectric film.

10. The method of claim 9 wherein the substantially aligned nanofibers of the first piezoelectric film are substantially parallel with the substantially aligned nanofibers of the second piezoelectric film, and are substantially perpendicular with the substantially aligned nanofibers of the third piezoelectric film.

11. The method of claim 5 wherein the compressible intervening layer is a hydrogel.

12. The method of claim 5 wherein upon identifying the cartilage or bone defect to be treated and prior to providing the implantable scaffold, at least one characteristic of the implantable scaffold is selected based on a characteristic of a patient in which the cartilage or bone defect was identified.

13. A method of treatment for osteoarthritis comprising:

identifying a cartilage or bone defect to be treated;

providing an implantable scaffold comprising a plurality of piezoelectric films and at least one compressible intervening layer between at least two of the plurality of piezoelectric films;

implanting the implantable scaffold adjacent the cartilage or bone defect to be treated and within a pinch point of a joint; and providing an exercise protocol for generating periodic impact at the pinch point, such that the periodic impact applies a mechanical force to a first piezoelectric film of the plurality of piezoelectric films such that the first piezoelectric film compresses the compressible intervening layer and deforms towards the second piezoelectric film, wherein upon identifying the cartilage or bone defect to be treated and prior to providing the implantable scaffold, at least one characteristic of the implantable scaffold is selected based on a characteristic of a patient in which the cartilage or bone defect was identified, and wherein at least one of a porosity of nanofibers of the plurality of piezoelectric films, a number of compressible intervening layers, and a thickness of at least one of the compressible intervening layers is selected based on a weight of the patient to tune the implantable scaffold.

* * * * *